US010884002B2

(12) United States Patent
Lombardi et al.

(10) Patent No.: US 10,884,002 B2
(45) Date of Patent: Jan. 5, 2021

(54) SIALYLATED FETUIN-A AS A MARKER OF IMMUNOTHERAPY EFFICACY

(71) Applicant: STALLERGENES, Antony (FR)

(72) Inventors: Vincent Lombardi, Antony (FR); Noémie Caillot, Paris (FR); Emmanuel Nony, Antony (FR); Philippe Moingeon, Verrieres le Buisson (FR); Véronique Bodo, Palaiseau (FR); Julien Bouley, Le Grand Lemps (FR)

(73) Assignee: STALLERGENES, Antony (FR)

( * ) Notice: Subject to any disclaimer, the term of this patent is extended or adjusted under 35 U.S.C. 154(b) by 624 days.

(21) Appl. No.: 15/528,250

(22) PCT Filed: Nov. 23, 2015

(86) PCT No.: PCT/EP2015/077360
§ 371 (c)(1),
(2) Date: May 19, 2017

(87) PCT Pub. No.: WO2016/079339
PCT Pub. Date: May 26, 2016

(65) Prior Publication Data
US 2017/0370946 A1 Dec. 28, 2017

(30) Foreign Application Priority Data
Nov. 21, 2014 (EP) .................................... 14306857

(51) Int. Cl.
| | | |
|---|---|---|
| *G01N 33/68* | (2006.01) | |
| *C07K 14/47* | (2006.01) | |
| *G01N 33/74* | (2006.01) | |
| *A61K 39/35* | (2006.01) | |
| *C07K 16/18* | (2006.01) | |
| *A61K 39/00* | (2006.01) | |
| *C12N 15/115* | (2010.01) | |

(52) U.S. Cl.
CPC ......... *G01N 33/6893* (2013.01); *A61K 39/35* (2013.01); *C07K 14/473* (2013.01); *C07K 14/4726* (2013.01); *C07K 16/18* (2013.01); *C12N 15/115* (2013.01); *G01N 33/74* (2013.01); *A61K 2039/541* (2013.01); *C12N 2310/16* (2013.01); *G01N 2333/4728* (2013.01); *G01N 2333/71* (2013.01); *G01N 2400/10* (2013.01); *G01N 2440/38* (2013.01); *G01N 2560/00* (2013.01); *G01N 2800/24* (2013.01); *G01N 2800/52* (2013.01)

(58) Field of Classification Search
None
See application file for complete search history.

(56) References Cited

U.S. PATENT DOCUMENTS 10,101,341 B2 * 10/2018 Bodo ................. G01N 33/6863

FOREIGN PATENT DOCUMENTS

| WO | 2012137180 A2 | 10/2012 |
|---|---|---|
| WO | 2012137180 A3 | 2/2013 |

OTHER PUBLICATIONS

R & D Systems "New Products Sep. 2009". pp. 1-12. Sep. 2009.*
Caillot et al. 'Sialylated Fetuin-A as a candidate predictive biomarker for successful grass pollen allergen immunotherapy.' J. Allergy Clin Immunolo. 140:759-770, 2017.*
Caillot et al. 'Sialylated Fetuin-A as a candidate predictive biomarker for successful grass pollen allergen immunotherapy.' J Allergy Clin Immunol. 140:759-70, 2017.*
Cieniewski-Bernard et al., Identification of O-linked N-acetylglucosamine proteins in rat skeletal muscle using two-dimensional gel electrophoresis ad mass spectrometry, The American Society far Biochemistry, and Molecular Biology, Inc., 577-585 (2004).
European Search Report dated May 29, 2015, for corresponding European Application No. EP 14306857.
Ashish Saroha et al., "Jacalin Bound Plasma O-Glycoproteorne and Reduced Sialylation of Alpha 2-HS Glycoprotein (A2HSG) in Rheumatoid Arthritis Patients", PLOS ONE, pp. 1-9, vol. 7, No. 10 (Oct. 2012).
Jincut Huang et al., "Glycomic Analysis of High Density Lipoprotein Shows a Highly Sialylated Particle" Journal of Proteome Research, pp. 681-691, vol. 13, No. 2 (Feb. 2014).
Signor L et al., "Two Dimensional Electrophoresis Protein Profiling and Identification in Rat Bronchoalvtolar Lavage Fluid Following Allergen and Endotoxin Challenge", Proteomics, pp. 2101-2110, vol. 4, No. 7 (Jul. 2004).

* cited by examiner

*Primary Examiner* — Nora M Rooney
(74) *Attorney, Agent, or Firm* — Browdy and Neimark, PLLC

(57) ABSTRACT

The invention concerns the identification of specific polypeptides, fragments variants thereof which can be used as markers for the efficacy of immunotherapy, particular for predicting responsiveness of a patient to immunotherapy.

8 Claims, 18 Drawing Sheets

Specification includes a Sequence Listing.

| Peptide | Mass (M+H⁺) (Da) | Sialic acid (Neu5Ac) | Sequence/PTM |
|---|---|---|---|
| OG1 | 8705.15 = 7392.7386 + (2 x 656.22) | 2 | LGGAEVAVTCTVFQTQPVTSQPQPEGANEAVPTPVVDPDAPPSPPLGAPGLPPAGSPPDSHVLLAAPPGHQLHR positions 256 and 270, each with GalNAc-Gal-NeuAc |
| OG2 | 8996.26 = 7392.7386 + (656.22 + 947.32) | 3 | LGGAEVAVTCTVFQTQPVTSQPQPEGANEAVPTPVVDPDAPPSPPLGAPGLPPAGSPPDSHVLLAAPPGHQLHR position 256 mono-sialylated core 1; position 270 di-sialylated core 1 |
| OG3 | 9287.36 = 7392.7386 + (2 x 947.32) | 4 | LGGAEVAVTCTVFQTQPVTSQPQPEGANEAVPTPVVDPDAPPSPPLGAPGLPPAGSPPDSHVLLAAPPGHQLHR positions 256 and 270, each di-sialylated core 1 |

FIG.4

A
ROC curve of OG3 abundance in active group with %ARTSS improvement = 50 as a cutoff
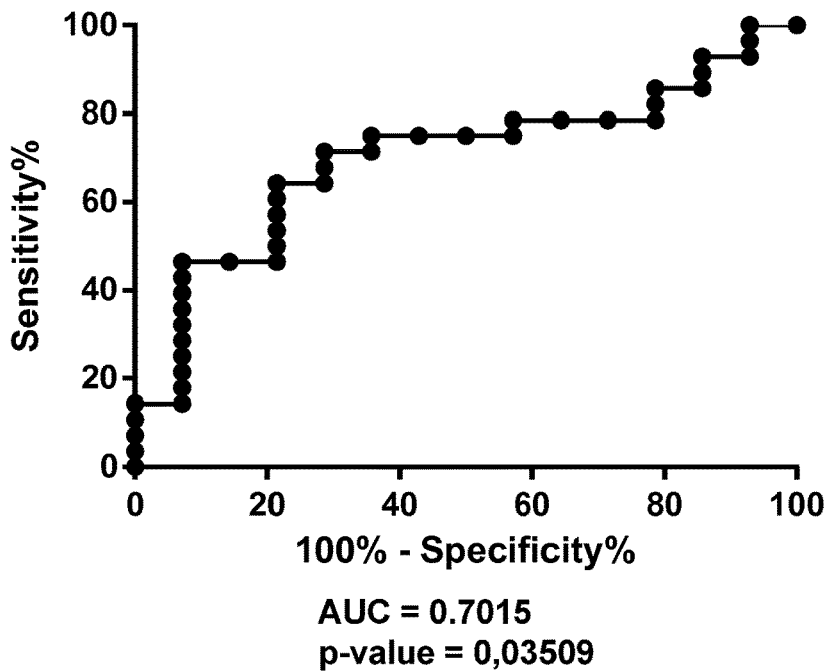
AUC = 0.7015
p-value = 0,03509
B
ROC curve of OG3 abundance in active group with %ARTSS improvement = 10 as a cutoff
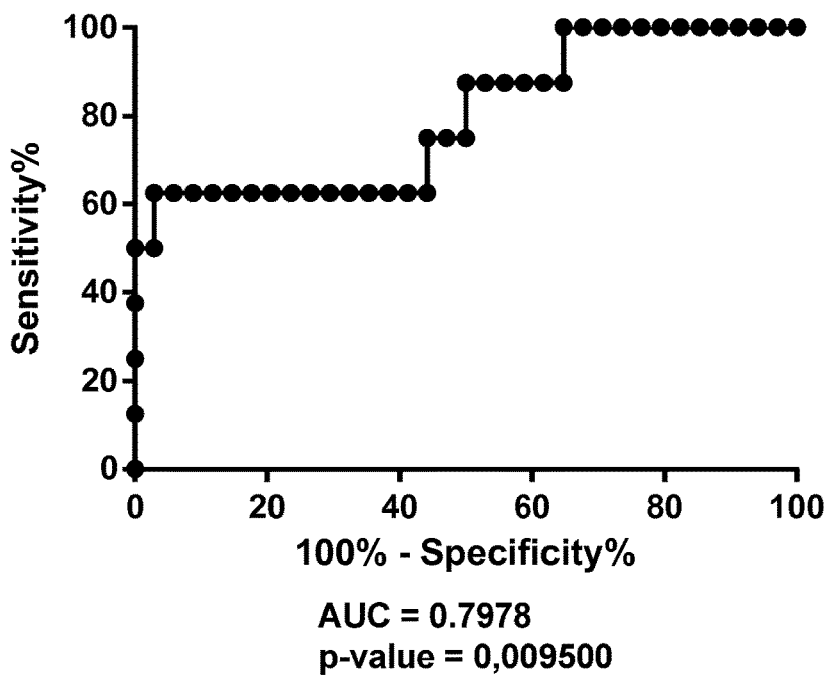
AUC = 0.7978
p-value = 0,009500
FIG.9 a
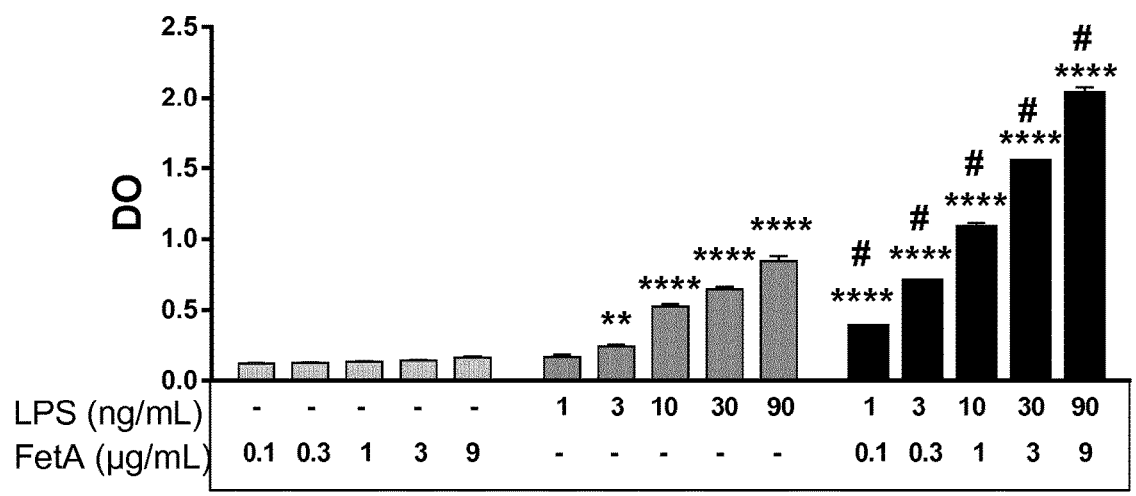
b
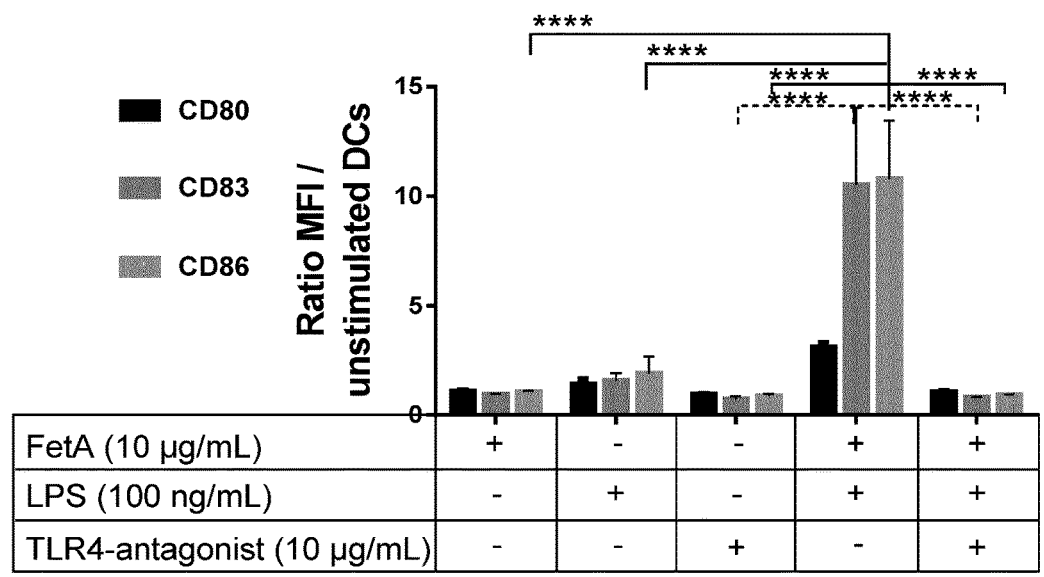
FIG. 11 (Beginning)

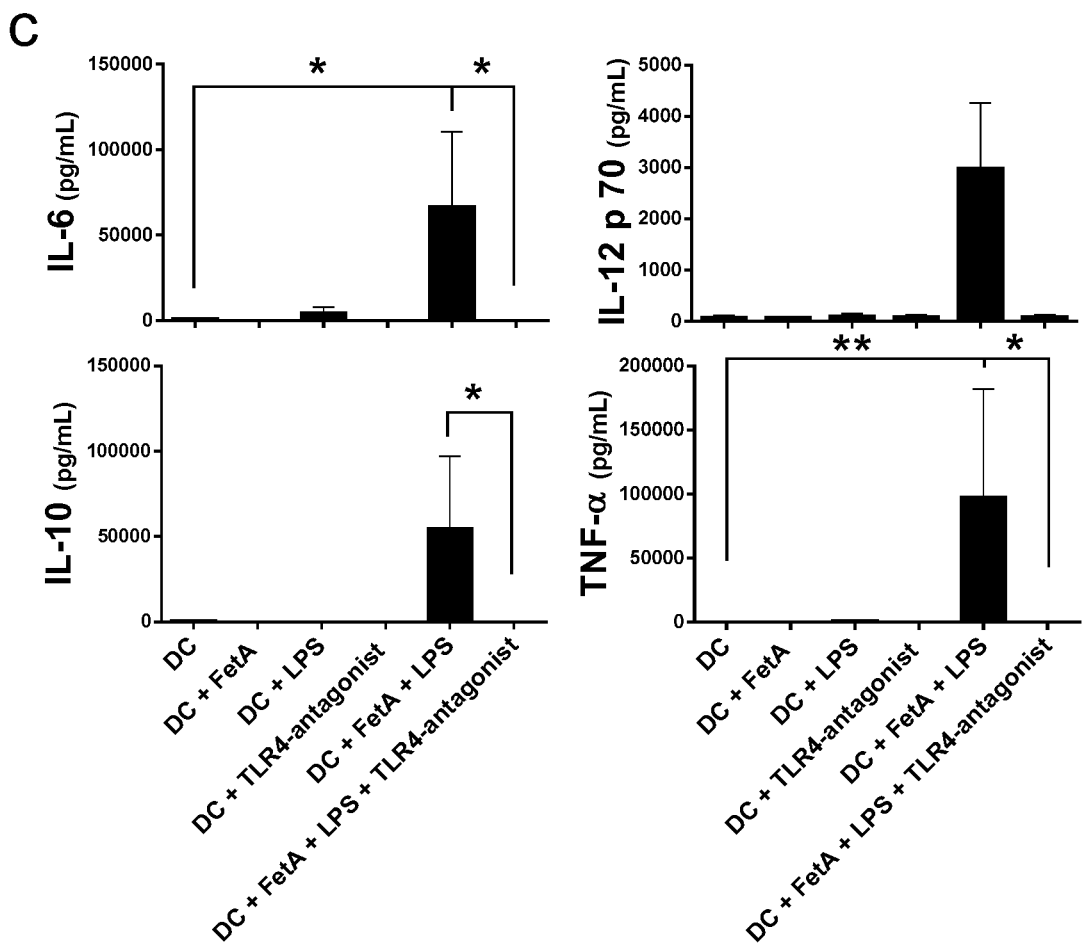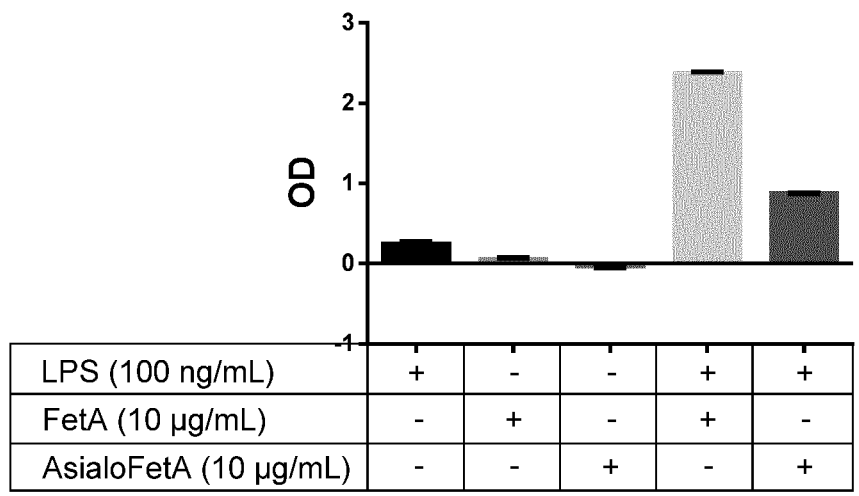
FIG.11 (Continuation)

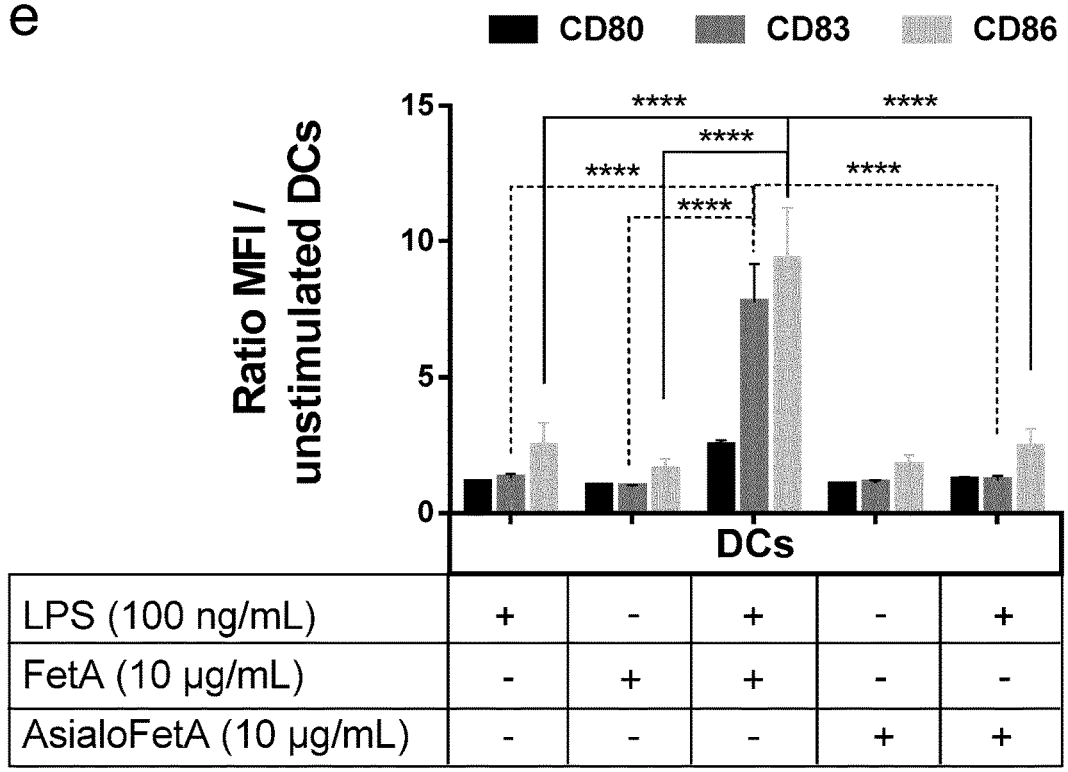
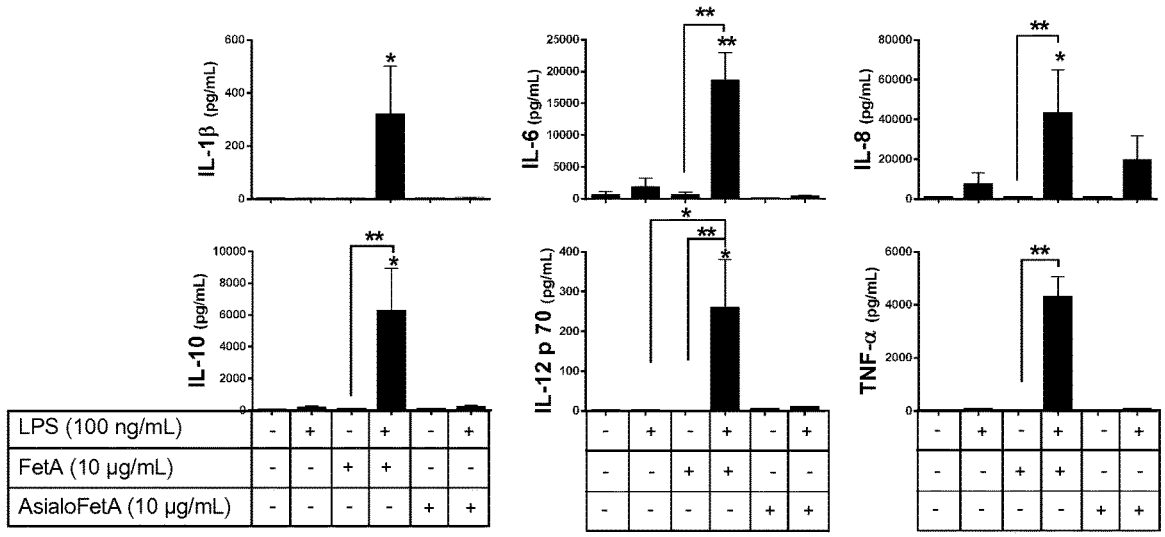
FIG.11 (End)

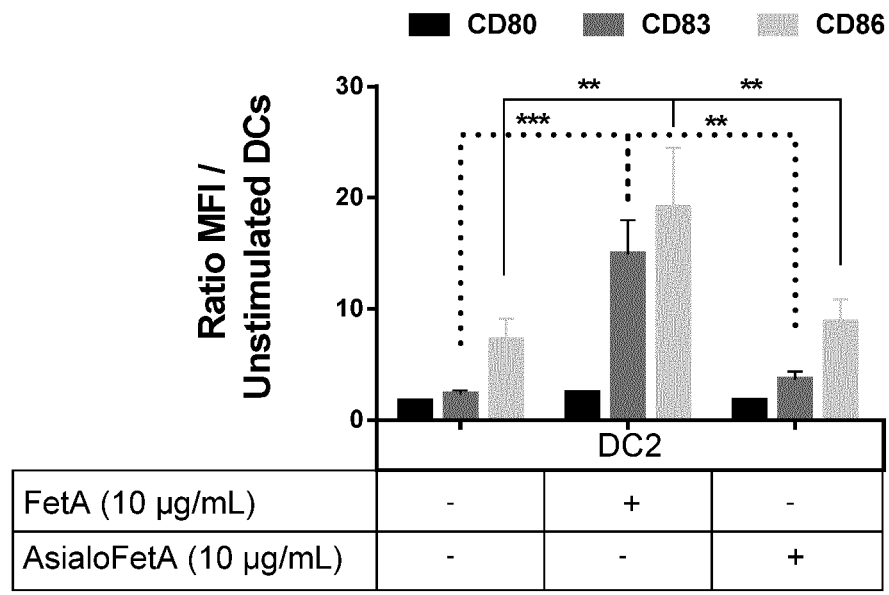
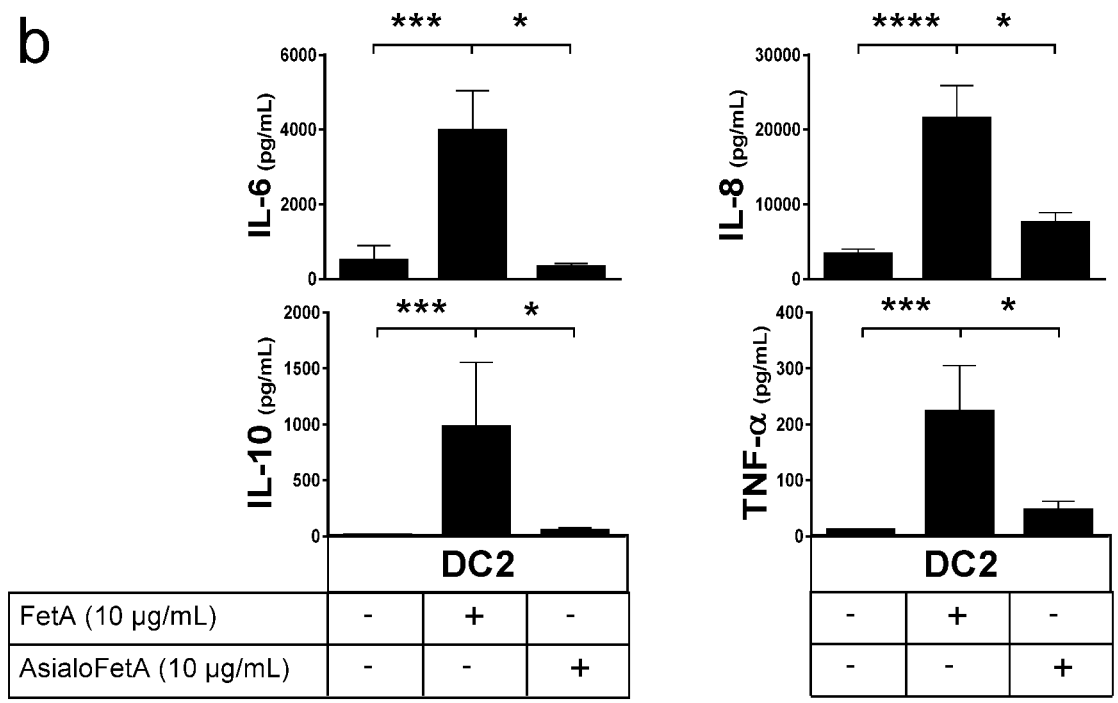
FIG.12 (Beginning)

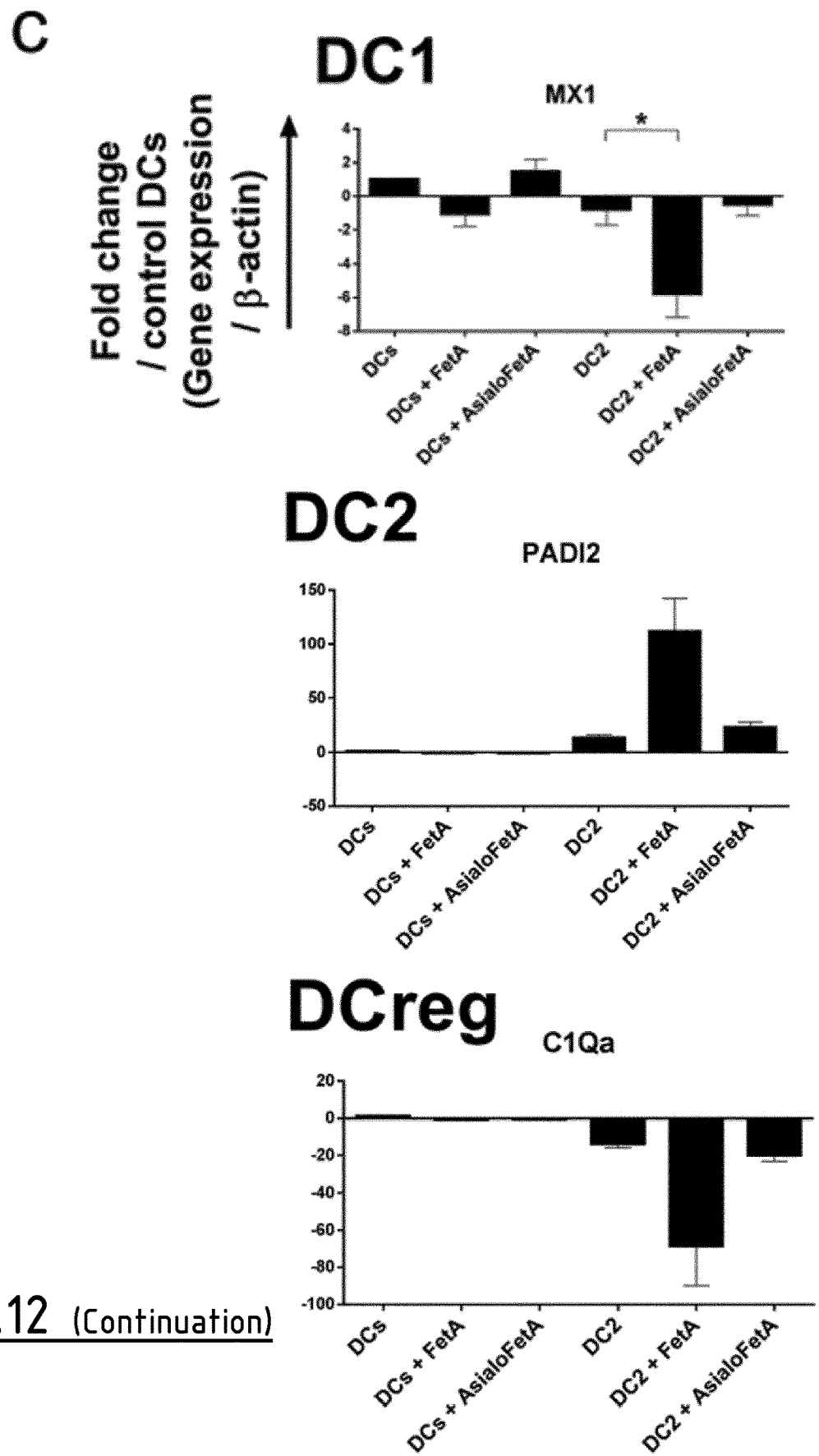
FIG.12 (Continuation)

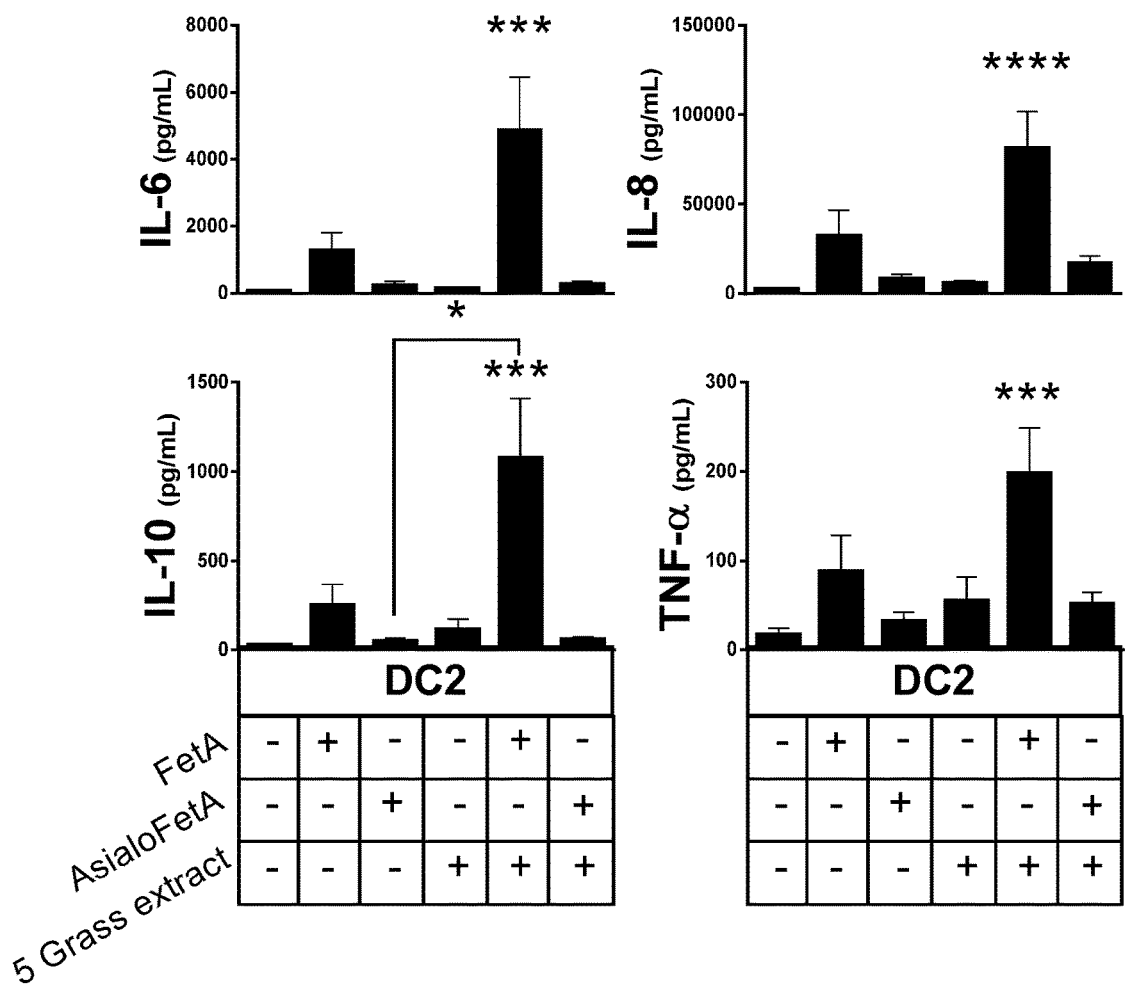
FIG.12 (Continuation)

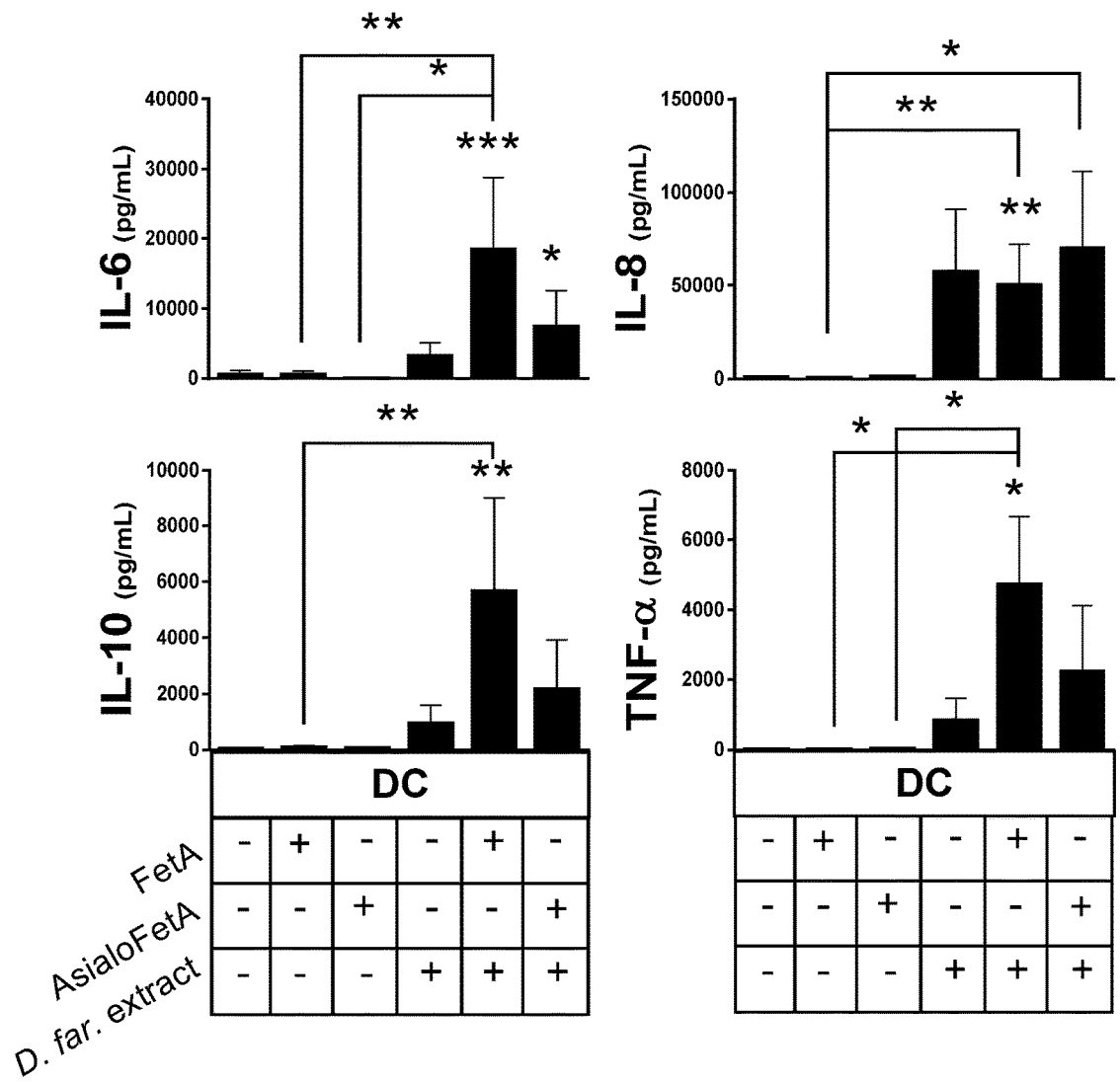
FIG. 12 (End)

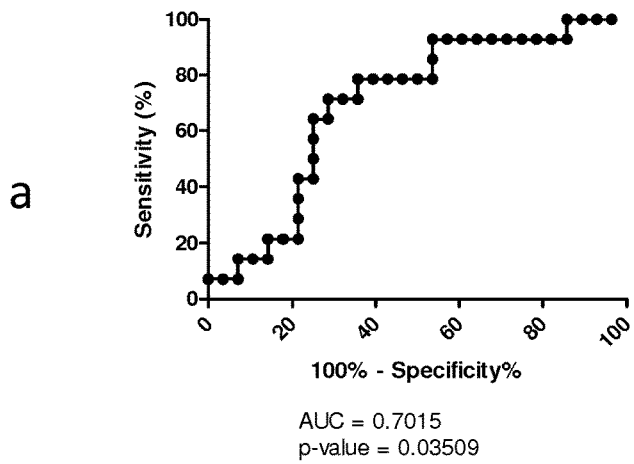
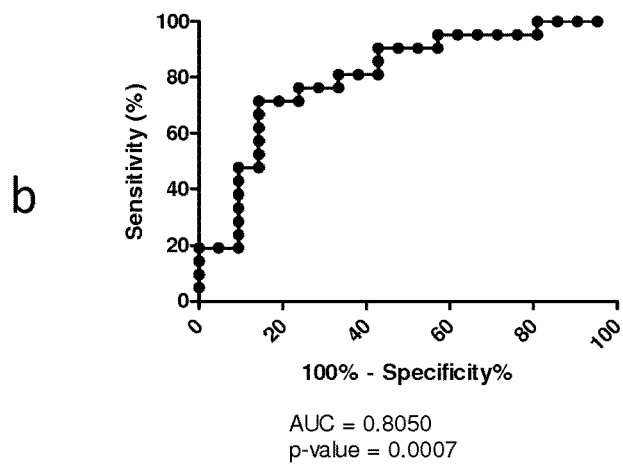
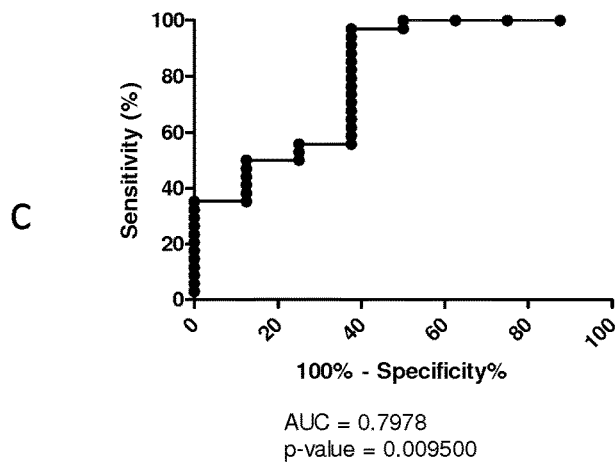
FIG.13

```
                        SEQUENCE LISTING

<160> NUMBER OF SEQ ID NOS: 30

<210> SEQ ID NO 1
<211> LENGTH: 367
<212> TYPE: PRT
<213> ORGANISM: Homo sapiens

<400> SEQUENCE: 1

Met Lys Ser Leu Val Leu Leu Cys Leu Ala Gln Leu Trp Gly Cys
1               5                   10                  15

His Ser Ala Pro His Gly Pro Gly Leu Ile Tyr Arg Gln Pro Asn Cys
                20                  25                  30

Asp Asp Pro Glu Thr Glu Glu Ala Ala Leu Val Ala Ile Asp Tyr Ile
            35                  40                  45

Asn Gln Asn Leu Pro Trp Gly Tyr Lys His Thr Leu Asn Gln Ile Asp
        50                  55                  60

Glu Val Lys Val Trp Pro Gln Gln Pro Ser Gly Glu Leu Phe Glu Ile
65                  70                  75                  80

Glu Ile Asp Thr Leu Glu Thr Thr Cys His Val Leu Asp Pro Thr Pro
                85                  90                  95

Val Ala Arg Cys Ser Val Arg Gln Leu Lys Glu His Ala Val Glu Gly
            100                 105                 110

Asp Cys Asp Phe Gln Leu Leu Lys Leu Asp Gly Lys Phe Ser Val Val
        115                 120                 125

Tyr Ala Lys Cys Asp Ser Ser Pro Asp Ser Ala Glu Asp Val Arg Lys
    130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
        195                 200                 205

Val Ala Lys Glu Ala Thr Glu Ala Ala Lys Cys Asn Leu Leu Ala Glu
    210                 215                 220

Lys Gln Tyr Gly Phe Cys Lys Ala Thr Leu Ser Glu Lys Leu Gly Gly
```

```
        225                 230                 235                 240
Ala Glu Val Ala Val Thr Cys Thr Val Phe Gln Thr Gln Pro Val Thr
                245                 250                 255

Ser Gln Pro Gln Pro Glu Gly Ala Asn Glu Ala Val Pro Thr Pro Val
                260                 265                 270

Val Asp Pro Asp Ala Pro Pro Ser Pro Pro Leu Gly Ala Pro Gly Leu
                275                 280                 285

Pro Pro Ala Gly Ser Pro Pro Asp Ser His Val Leu Leu Ala Ala Pro
                290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
                340                 345                 350

Pro Val Val Pro Pro Cys Pro Gly Arg Ile Arg His Phe Lys Val
                355                 360                 365
```

<210> SEQ ID NO 2
<211> LENGTH: 74
<212> TYPE: PRT
<213> ORGANISM: Homo sapiens

<400> SEQUENCE: 2

```
Leu Gly Gly Ala Glu Val Ala Val Thr Cys Thr Val Phe Gln Thr Gln
1               5                   10                  15

Pro Val Thr Ser Gln Pro Gln Pro Glu Gly Ala Asn Glu Ala Val Pro
                20                  25                  30

Thr Pro Val Val Asp Pro Asp Ala Pro Pro Ser Pro Pro Leu Gly Ala
                35                  40                  45

Pro Gly Leu Pro Pro Ala Gly Ser Pro Pro Asp Ser His Val Leu Leu
                50                  55                  60

Ala Ala Pro Pro Gly His Gln Leu His Arg
65                  70
```

<210> SEQ ID NO 3
<211> LENGTH: 5
<212> TYPE: PRT
<213> ORGANISM: Homo sapiens

<400> SEQUENCE: 3

```
Val Thr Ser Gln Pro
1               5
```

<210> SEQ ID NO 4
<211> LENGTH: 5
<212> TYPE: PRT
<213> ORGANISM: Homo sapiens

<400> SEQUENCE: 4

```
Val Pro Thr Pro Val
1               5
```

<210> SEQ ID NO 5
<211> LENGTH: 40
<212> TYPE: PRT
<213> ORGANISM: Homo sapiens

<400> SEQUENCE: 5

```
Ala Pro His Gly Pro Gly Leu Ile Tyr Arg Gln Pro Asn Cys Asp
1               5                   10                  15

Pro Glu Thr Glu Glu Ala Ala Leu Val Ala Ile Asp Tyr Ile Asn Gln
            20                  25                  30

Asn Leu Pro Trp Gly Tyr Lys His
        35                  40

<210> SEQ ID NO 6
<211> LENGTH: 39
<212> TYPE: PRT
<213> ORGANISM: Homo sapiens

<400> SEQUENCE: 6

Pro His Gly Pro Gly Leu Ile Tyr Arg Gln Pro Asn Cys Asp Asp Pro
1               5                   10                  15

Glu Thr Glu Glu Ala Ala Leu Val Ala Ile Asp Tyr Ile Asn Gln Asn
            20                  25                  30

Leu Pro Trp Gly Tyr Lys His
        35

<210> SEQ ID NO 7
<211> LENGTH: 31
<212> TYPE: PRT
<213> ORGANISM: Homo sapiens

<400> SEQUENCE: 7

Arg Gln Pro Asn Cys Asp Asp Pro Glu Thr Glu Glu Ala Ala Leu Val
1               5                   10                  15

Ala Ile Asp Tyr Ile Asn Gln Asn Leu Pro Trp Gly Tyr Lys His
            20                  25                  30

<210> SEQ ID NO 8
<211> LENGTH: 41
<212> TYPE: PRT
<213> ORGANISM: Homo sapiens

<400> SEQUENCE: 8

Arg Gln Pro Asn Cys Asp Asp Pro Glu Thr Glu Glu Ala Ala Leu Val
1               5                   10                  15

Ala Ile Asp Tyr Ile Asn Gln Asn Leu Pro Trp Gly Tyr Lys His Thr
            20                  25                  30

Leu Asn Gln Ile Asp Glu Val Lys Val
        35                  40

<210> SEQ ID NO 9
<211> LENGTH: 25
<212> TYPE: PRT
<213> ORGANISM: Homo sapiens

<400> SEQUENCE: 9

Asp Pro Glu Thr Glu Glu Ala Ala Leu Val Ala Ile Asp Tyr Ile Asn
1               5                   10                  15

Gln Asn Leu Pro Trp Gly Tyr Lys His
            20                  25

<210> SEQ ID NO 10
<211> LENGTH: 44
<212> TYPE: PRT
<213> ORGANISM: Homo sapiens

<400> SEQUENCE: 10
```

```
Lys His Thr Leu Asn Gln Ile Asp Glu Val Lys Val Trp Pro Gln Gln
1               5                   10                  15
Pro Ser Gly Glu Leu Phe Glu Ile Glu Ile Asp Thr Leu Glu Thr Thr
            20                  25                  30
Cys His Val Leu Asp Pro Thr Pro Val Ala Arg Cys
        35                  40
```

<210> SEQ ID NO 11
<211> LENGTH: 40
<212> TYPE: PRT
<213> ORGANISM: Homo sapiens

<400> SEQUENCE: 11

```
Asn Gln Ile Asp Glu Val Lys Val Trp Pro Gln Gln Pro Ser Gly Glu
1               5                   10                  15
Leu Phe Glu Ile Glu Ile Asp Thr Leu Glu Thr Thr Cys His Val Leu
            20                  25                  30
Asp Pro Thr Pro Val Ala Arg Cys
        35                  40
```

<210> SEQ ID NO 12
<211> LENGTH: 19
<212> TYPE: PRT
<213> ORGANISM: Homo sapiens

<400> SEQUENCE: 12

```
Arg Gln Leu Lys Glu His Ala Val Glu Gly Asp Cys Asp Phe Gln Leu
1               5                   10                  15
Leu Lys Leu
```

<210> SEQ ID NO 13
<211> LENGTH: 16
<212> TYPE: PRT
<213> ORGANISM: Homo sapiens

<400> SEQUENCE: 13

```
Lys Glu His Ala Val Glu Gly Asp Cys Asp Phe Gln Leu Leu Lys Leu
1               5                   10                  15
```

<210> SEQ ID NO 14
<211> LENGTH: 20
<212> TYPE: PRT
<213> ORGANISM: Homo sapiens

<400> SEQUENCE: 14

```
Lys Glu His Ala Val Glu Gly Asp Cys Asp Phe Gln Leu Leu Lys Leu
1               5                   10                  15
Asp Gly Lys Phe
            20
```

<210> SEQ ID NO 15
<211> LENGTH: 9
<212> TYPE: PRT
<213> ORGANISM: Homo sapiens

<400> SEQUENCE: 15

```
Lys Phe Ser Val Val Tyr Ala Lys Cys
1               5
```

<210> SEQ ID NO 16
<211> LENGTH: 17
<212> TYPE: PRT

-continued

```
<213> ORGANISM: Homo sapiens

<400> SEQUENCE: 16

Lys Val Cys Gln Asp Cys Pro Leu Leu Ala Pro Leu Asn Asp Thr Arg
1               5                   10                  15

Val

<210> SEQ ID NO 17
<211> LENGTH: 24
<212> TYPE: PRT
<213> ORGANISM: Homo sapiens

<400> SEQUENCE: 17

Lys Ala Ala Leu Ala Ala Phe Asn Ala Gln Asn Asn Gly Ser Asn Phe
1               5                   10                  15

Gln Leu Glu Glu Ile Ser Arg Ala
            20

<210> SEQ ID NO 18
<211> LENGTH: 26
<212> TYPE: PRT
<213> ORGANISM: Homo sapiens

<400> SEQUENCE: 18

Arg Ala Gln Leu Val Pro Leu Pro Pro Ser Thr Tyr Val Glu Phe Thr
1               5                   10                  15

Val Ser Gly Thr Asp Cys Val Ala Lys Glu
            20                  25

<210> SEQ ID NO 19
<211> LENGTH: 33
<212> TYPE: PRT
<213> ORGANISM: Homo sapiens

<400> SEQUENCE: 19

Arg Ala Gln Leu Val Pro Leu Pro Pro Ser Thr Tyr Val Glu Phe Thr
1               5                   10                  15

Val Ser Gly Thr Asp Cys Val Ala Lys Glu Ala Thr Glu Ala Ala Lys
            20                  25                  30

Cys

<210> SEQ ID NO 20
<211> LENGTH: 9
<212> TYPE: PRT
<213> ORGANISM: Homo sapiens

<400> SEQUENCE: 20

Lys Cys Asn Leu Leu Ala Glu Lys Gln
1               5

<210> SEQ ID NO 21
<211> LENGTH: 8
<212> TYPE: PRT
<213> ORGANISM: Homo sapiens

<400> SEQUENCE: 21

Lys Gln Tyr Gly Phe Cys Lys Ala
1               5

<210> SEQ ID NO 22
<211> LENGTH: 39
<212> TYPE: PRT
```

<213> ORGANISM: Homo sapiens

<400> SEQUENCE: 22

Asp Pro Asp Ala Pro Ser Pro Pro Leu Gly Ala Pro Gly Leu Pro
1               5                   10                  15

Pro Ala Gly Ser Pro Pro Asp Ser His Val Leu Leu Ala Ala Pro Pro
                20                  25                  30

Gly His Gln Leu His Arg Ala
            35

<210> SEQ ID NO 23
<211> LENGTH: 8
<212> TYPE: PRT
<213> ORGANISM: Homo sapiens

<400> SEQUENCE: 23

Arg Ala His Tyr Asp Leu Arg His
1               5

<210> SEQ ID NO 24
<211> LENGTH: 28
<212> TYPE: PRT
<213> ORGANISM: Homo sapiens

<400> SEQUENCE: 24

Arg Ala His Tyr Asp Leu Arg His Thr Phe Met Gly Val Val Ser Leu
1               5                   10                  15

Gly Ser Pro Ser Gly Glu Val Ser His Pro Arg Lys
                20                  25

<210> SEQ ID NO 25
<211> LENGTH: 21
<212> TYPE: PRT
<213> ORGANISM: Homo sapiens

<400> SEQUENCE: 25

Arg His Thr Phe Met Gly Val Val Ser Leu Gly Ser Pro Ser Gly Glu
1               5                   10                  15

Val Ser His Pro Arg
                20

<210> SEQ ID NO 26
<211> LENGTH: 22
<212> TYPE: PRT
<213> ORGANISM: Homo sapiens

<400> SEQUENCE: 26

Arg His Thr Phe Met Gly Val Val Ser Leu Gly Ser Pro Ser Gly Glu
1               5                   10                  15

Val Ser His Pro Arg Lys
                20

<210> SEQ ID NO 27
<211> LENGTH: 23
<212> TYPE: PRT
<213> ORGANISM: Homo sapiens

<400> SEQUENCE: 27

Arg His Thr Phe Met Gly Val Val Ser Leu Gly Ser Pro Ser Gly Glu
1               5                   10                  15

Val Ser His Pro Arg Lys Thr
                20

```
<210> SEQ ID NO 28
<211> LENGTH: 23
<212> TYPE: PRT
<213> ORGANISM: Homo sapiens

<400> SEQUENCE: 28

Arg Thr Val Val Gln Pro Ser Val Gly Ala Ala Ala Gly Pro Val Val
1               5                   10                  15

Pro Pro Cys Pro Gly Arg Ile
            20

<210> SEQ ID NO 29
<211> LENGTH: 22
<212> TYPE: PRT
<213> ORGANISM: Homo sapiens

<400> SEQUENCE: 29

Thr Val Val Gln Pro Ser Val Gly Ala Ala Ala Gly Pro Val Val Pro
1               5                   10                  15

Pro Cys Pro Gly Arg Ile
            20

<210> SEQ ID NO 30
<211> LENGTH: 21
<212> TYPE: PRT
<213> ORGANISM: Homo sapiens

<400> SEQUENCE: 30

Val Val Gln Pro Ser Val Gly Ala Ala Ala Gly Pro Val Val Pro Pro
1               5                   10                  15

Cys Pro Gly Arg Ile
            20
```

SIALYLATED FETUIN-A AS A MARKER OF IMMUNOTHERAPY EFFICACY

The invention concerns new markers for the efficacy of immunotherapy, in particular for predicting responsiveness of a patient to immunotherapy.

BACKGROUND OF THE INVENTION

Allergy is a major and growing health concern around the world. As societies become more affluent and reduce the incidence of contagious disease, the prevalence of allergic disease increases. Finding effective treatments for allergy, both preventive and therapeutic, is a growing challenge for today's healthcare industry. Traditionally, management of allergy has concentrated on alleviation of symptoms, using anti-histamines and medications which relieve allergic symptoms including nasal congestion, dermatitis and asthma, such as decongestants, creams, anti-inflammatories and bronchodilators. Allergen avoidance is another strategy for allergy management, but this is often difficult or impossible, particularly in the case of pervasive allergens such as pollen. A third alternative is specific allergy vaccination, in which patients are administered with the allergen causing the allergy in order to obtain an improvement in the patient's immune status. This kind of treatment has the advantage of altering the course of the illness to prevent the manifestation of symptoms, rather than simply alleviating symptoms.

Allergen immunotherapy (AIT) is an efficacious therapy for type I respiratory allergies or allergy. Injective immunotherapy (subcutaneous immunotherapy or SCIT) was first reported in 1911 and has been used in clinical practice since the 1970s. Immunotherapy via administration of allergen to mucosa, such as the oral mucosa of the mouth and gut, has also been explored. Sublingual immunotherapy (SLIT), in which vaccine is administered underneath the tongue and absorbed via the sublingual mucosa, is a well-established alternative to injective immunotherapy. Allergen immunotherapy performed via the subcutaneous or sublingual route is currently established as a safe and efficacious treatment for allergies, with a disease modifying effect. However, not all the patients treated with immunotherapy will experience reduction of symptoms. Identifying methods of selecting patients likely to respond well to immunotherapy is thus of interest.

The WO2012/137180 patent application discloses a list of biomarkers of immunotherapy efficacy, among which Fetuin-A. Different isoforms of Fetuin-A are observed, however, this document indicates that the proportion of sialic acid relative to the neutral sugars does not appear to account for the separation of the isoforms. Conversely, this document suggests that Fetuin-A polypeptide comprising a phosphorylated serine 330 may be a biomarker of immunotherapy efficacy of particular interest.

Huang et al., Journal of Proteome research, 2014, 13, 681-691 describes the glycosylation patterns of Fetuin-A. However, the function(s) in which these glycosylations are involved is unknown.

Saroha et al., PlosOne, 2012, 7 discloses that patients with rheumatoid arthritis have reduced sialylation of N-glycans of Fetuin-A in plasma. However, no correlation is made concerning O-glycans sites.

The inventors have shown that Fetuin-A polypeptides, or fragments thereof, bearing specific post-translational modifications are expressed at a higher level in patients who responded well to allergen immunotherapy for grass pollen allergy than in patients who responded less well. These polypeptides thus have potential as markers for efficacy of immunotherapy, in particular as predictive markers for use in selecting patients who will respond to immunotherapy.

The inventors have also shown that sialylated Fetuin-A enhances TLR4-mediated allergic inflammation, thereby enhancing Th2 inflammatory responses to grass pollen or house dust mite. A high degree of Fetuin-A sialylation would reflect a susceptibility of higher allergic response. It is however known that higher symptom severity correlates with clinical improvement during immunotherapy.

In its broadest aspect, the invention relates to the use of Fetuin-A polypeptides, or fragments thereof, bearing specific post-translational modifications, as markers for the efficacy of immunotherapy. In a preferred embodiment, the marker protein is used to predict the responsiveness of a patient to immunotherapy. In another embodiment, the marker protein is used to select patients as suitable candidates for immunotherapy.

SUMMARY OF THE INVENTION

Thus, the invention provides a method for predicting responsiveness of a patient to immunotherapy, which method comprises detecting the level of expression of a Fetuin-A polypeptide, or a fragment thereof, comprising an O-linked oligosaccharide chain bearing two terminal sialic acid residues at position 256 and/or an O-linked oligosaccharide chain bearing two terminal sialic acid residues at position 270, by reference to the amino acid positions as shown in sequence SEQ ID NO: 1, in a biological sample from said patient, wherein said biological sample is taken before the commencement of and/or during immunotherapy, and wherein said immunotherapy comprises administration of an allergen or auto-antigen to said patient in order to treat allergy or auto-immune disease.

The invention also provides a method for predicting responsiveness of a patient to immunotherapy, which method comprises detecting the level of expression of a Fetuin-A polypeptide, or a fragment thereof, comprising an O-linked oligosaccharide chain bearing two terminal sialic acid residues at position 270 and an O-linked oligosaccharide chain bearing one or two terminal sialic acid residues at position 256, by reference to the amino acid positions as shown in sequence SEQ ID NO: 1, in a biological sample from said patient, wherein said biological sample is taken before the commencement of and/or during immunotherapy, and wherein said immunotherapy comprises administration of an allergen or auto-antigen to said patient in order to treat allergy or auto-immune disease.

The invention moreover provides a method for selecting a patient for immunotherapy, which method comprises the steps of:
 a) detecting the level of expression of a Fetuin-A polypeptide, or a fragment thereof, comprising an O-linked oligosaccharide chain bearing two terminal sialic acid residues at position 256 and/or comprising an O-linked oligosaccharide chain bearing two terminal sialic acid residues at position 270, by reference to the amino acid positions as shown in sequence SEQ ID NO: 1, in a biological sample from said patient;
 b) comparing said level of expression with a control;
 c) selecting or rejecting said patient for immunotherapy based on the comparison with the control;
wherein said biological sample is taken before the commencement of immunotherapy, and wherein said immunotherapy comprises administration of an allergen or autoantigen to said patient in order to treat allergy or autoimmune disease.

The invention further provides a method for selecting a patient for immunotherapy, which method comprises the steps of:

a) detecting the level of expression of a Fetuin-A polypeptide, or a fragment thereof, comprising an O-linked oligosaccharide chain bearing two terminal sialic acid residues at position 270 and comprising an O-linked oligosaccharide chain bearing one or two terminal sialic acid residues at position 256, by reference to the amino acid positions as shown in sequence SEQ ID NO: 1, in a biological sample from said patient;

b) comparing said level of expression with a control;

c) selecting or rejecting said patient for immunotherapy based on the comparison with the control;

wherein said biological sample is taken before the commencement of immunotherapy, and wherein said immunotherapy comprises administration of an allergen or autoantigen to said patient in order to treat allergy or autoimmune disease.

Further provided is an allergen or auto-antigen for use for immunotherapy in a patient selected for immunotherapy, comprising selecting the patient for immunotherapy by implementing the method for selecting a patient for immunotherapy according to the invention.

Also disclosed herein is a method for treating a patient by immunotherapy which comprises the steps of:

1) selecting a patient for immunotherapy by:

a) detecting the level of expression of a Fetuin-A polypeptide, or a fragment thereof, comprising an O-linked oligosaccharide chain bearing two terminal sialic acid residues at position 256 and/or comprising an O-linked oligosaccharide chain bearing two terminal sialic acid residues at position 270, by reference to the amino acid positions as shown in sequence SEQ ID NO: 1, in a biological sample from said patient;

b) comparing said level of expression with a control;

c) selecting or rejecting said patient for immunotherapy based on the comparison with the control;

wherein said biological sample is taken before the commencement of immunotherapy, and wherein said immunotherapy comprises administration of an allergen or autoantigen to said patient in order to treat allergy or autoimmune disease; and 2) administering said allergen or auto-antigen to said patient if the patient is selected at step c).

Further disclosed is a method for treating a patient by immunotherapy which comprises the steps of:

1) selecting a patient for immunotherapy by:

a) detecting the level of expression of a Fetuin-A polypeptide, or a fragment thereof, comprising an O-linked oligosaccharide chain bearing two terminal sialic acid residues at position 270 and an O-linked oligosaccharide chain bearing one or two terminal sialic acid residues at position 256, by reference to the amino acid positions as shown in sequence SEQ ID NO: 1, in a biological sample from said patient;

b) comparing said level of expression with a control;

c) selecting or rejecting said patient for immunotherapy based on the comparison with the control;

wherein said biological sample is taken before the commencement of immunotherapy, and wherein said immunotherapy comprises administration of an allergen or autoantigen to said patient in order to treat allergy or autoimmune disease; and 2) administering said allergen or auto-antigen to said patient if the patient is selected at step c).

According to a specific embodiment, the immunotherapy comprises administration of allergen to a mucosal surface, optionally a sublingual, oral, buccal, ocular, rectal, urinal, pulmonal or ear surface, or administration of allergen via a subcutaneous, intranasal, transdermal, intralymphatic route or epicutaneous route.

According to another embodiment, said immunotherapy comprises administration of an allergen extract.

The invention further provides an isolated antibody, a lectin, or an aptamer, which binds specifically to a Fetuin-A polypeptide, or a fragment thereof, as defined in the present application.

The invention also concerns a peptide of sequence SEQ ID NO: 2 bearing an O-linked oligosaccharide chain bearing two terminal sialic acid residues at position 256 and an O-linked oligosaccharide chain associated with two terminal sialic acid residues at position 270, by reference to the amino acid positions as shown in sequence SEQ ID NO: 1.

The invention further concerns a peptide of sequence SEQ ID NO: 2 bearing an O-linked oligosaccharide chain bearing one terminal sialic acid residue at position 256 and an O-linked oligosaccharide chain associated with two terminal sialic acid residues at position 270, by reference to the amino acid positions as shown in sequence SEQ ID NO: 1.

The invention finally relates to the use of a calibration standard protein of sequence SEQ ID NO: 1, of a peptide of sequence SEQ ID NO: 2, of a peptide of sequence SEQ ID NO: 3 or of a peptide of sequence SEQ ID NO: 4, optionally labeled with one or more mass-modifying labeling agent, for the quantification of the absolute amount of, respectively, the protein of sequence SEQ ID NO: 1, the peptide of sequence SEQ ID NO: 2, the peptide of sequence SEQ ID NO: 3 or the peptide of sequence SEQ ID NO:4.

DESCRIPTION OF THE INVENTION

Fetuin-A Polypeptides or Fragments Thereof

Fetuin-A is also known as alpha-2-HS-glycoprotein, alpha-2-Z-globulin, or Ba-alpha-2-glycoprotein. As used herein, Fetuin-A refers to the protein having Swiss-Prot accession number FETUA_HUMAN, and/or referenced as P02765 in the UniProtKB/Swiss-Prot database on Oct. 20, 2014, and/or the polypeptide consisting of the amino acid sequence below:

```
                                         (SEQ ID NO: 1)
₁MKSLVLLLCLAQLWGCHSAPHGPGLIYRQPNCDDPETEEAALVAIDYIN

QNLPWGYKHTLNQIDEVKVWPQQPSGELFEIEIDTLETTCHVLDPTPVAR

CSVRQLKEHAVEGDCDFQLLKLDGKFSVVYAKCDSSPDSAEDVRKVCQDC

PLLAPLNDTRVVHAAKAALAAFNAQNNGSNFQLEEISRAQLVPLPPSTYV

EFTVSGTDCVAKEATEAAKCNLLAEKQYGFCKATLSEKLGGAEVAVTCTV

FQTQPVTSQPQPEGANEAVPTPVVDPDAPPSPPLGAPGLPPAGSPPDSHV

LLAAPPGHQLHRAHYDLRHTFMGVVSLGSPSGEVSHPRKTRTVVQPSVGA

AAGPVVPPCPGRIRHFKV₃₆₇.
```

The term 'Fetuin-A polypeptide' includes the polypeptide comprising or consisting of the amino acid sequence of SEQ ID NO: 1 and all variants thereof.

The term 'Variants', or 'isoforms' which may be used indifferently, refers to all alternative forms of a polypeptide, for example naturally occurring variants, allelic variants, SNPs (single nucleotide polymorphisms), alternative splice variants, truncated or secreted forms of the polypeptide, and post-translationally modified forms.

The variant may differ from SEQ ID NO: 1 by one or more modifications, such as i.e. addition, deletion and/or substitution, of one or more amino acids. The polypeptide of the invention may for instance differ from SEQ ID NO: 1 by 1, 2, 3, 4, 5, 6, 7, 8, 9, 10, 12, 15, 20, or 30 amino acids.

The variant preferably comprises, or consists of, a sequence at least 70%, 75%, 80%, 85%, 86%, 87%, 88%, 89%, 90%, 91%, 92%, 93%, 94%, 95%, 96%, 97%, 98%, or 99% identical to the sequence SEQ ID NO: 1 and preferably has a same biological activity as the polypeptide of sequence SEQ ID NO: 1. By a polypeptide consisting of an amino acid sequence at least, for example, 95% "identical" to the sequence SEQ ID NO: 1, it is intended that the amino acid sequence of the polypeptide, after global pairwise alignment with the sequence SEQ ID NO: 1, the polypeptide sequence may include up to five amino acid modifications per each 100 amino acids of the sequence SEQ ID NO: 1. In other words, to obtain a polypeptide consisting of an amino acid sequence at least 95% identical to the sequence SEQ ID NO: 1, up to 5% (5 of 100) of the amino acid residues in the subject sequence may be inserted, deleted, or substituted with another amino acid. The percentage of identity between two sequences may be determined by global pairwise alignment using the Needleman-Wunsch algorithm. The percentage of sequence identity can be readily determined for instance using the program Needle, with the BLOSUM62 matrix, and the following parameters gap-open=10, gap-extend=0.5. A "same biological activity" may denote a same biological function. Therefore, in the context of the invention, a polypeptide having a same biological activity as the polypeptide of sequence SEQ ID NO: 1 may for instance be a polypeptide exhibiting pro or anti-inflammatory function, or inhibiting the insulin or TGF-β signalling, or inhibiting pathological calcifications. The activity of a polypeptide can easily be evaluated in vitro or in vivo by the person skilled in the art.

Post-translationally modified variants may include acetylated, formylated, lipoylated, myristoylated, palmitoylated, alkylated, methylated, amidated, glycosylated, hydroxylated, nitrosylated, phosphorylated, sulphated, polysialylated and sialylated forms.

Known Fetuin-A polypeptide variants or isoforms are disclosed at www.uniprot.org/uniprot/P02765. They include post-translational modifications such as isoforms including phosphoserine at residue(s) 134, 138, 325, 328, 330 and/or 334; N-linked GlcNAc at residue(s) 156 and/or 176; O-linked GlcNAc at position(s) 256, 270 and/or 346; disulphide bonds between positions 32 and 358, 89 and 100, 114 and 132, 146 and 149, 208 and 219, 230 and 247; natural variants such as the substitution mutants V142L, T248M, T256S, D276N, R317C; pre- and processed forms comprising or lacking one or more of: the signal peptide (residues 1-18), the A chain (residues 19-300), the B chain (residues 341-367) and the connecting peptide (residues 301-340).

In the context of the invention, the numbering of amino acid positions in a Fetuin-A polypeptide is determined by global pairwise alignment of said polypeptide with the sequence SEQ ID NO: 1, and by taking SEQ ID NO: 1 as a reference sequence for the numbering of amino acid positions. Thus, an amino acid located on said polypeptide sequence at a position corresponding to the amino acid position N on the sequence SEQ ID NO: 1, as determined by global pairwise alignment of said polypeptide with the sequence SEQ ID NO: 1, is considered to be at position N on said polypeptide sequence. While taking SEQ ID NO: 1 as a reference sequence for the numbering of amino acid positions, as described herein, the Fetuin-A polypeptide or fragment thereof comprises an O-linked oligosaccharide chain bearing two terminal sialic acid residues at position 256. In a preferred embodiment, the Fetuin-A polypeptide or fragment thereof further comprises an O-linked oligosaccharide chain bearing two terminal sialic acid residues at position 270.

A 'fragment' of a Fetuin-A polypeptide sequence refers to a stretch of contiguous amino acids of said polypeptide sequence which is shorter than the complete polypeptide sequence. In particular a fragment may consist of at least 4, 5, 6, 7, 8, 9, 10, 11, 12, 13, 14, 15, 20, 25, 30, 35, or 40 consecutive amino acids of said polypeptide sequence. Preferably, a fragment contains no more than 350, 300, 250, 200, 150, 100, 50, or 25 consecutive amino acids of said polypeptide sequence.

In a preferred embodiment, the fragment of Fetuin-A is a polypeptide comprising or consisting of the following sequence:
$_{238}$LGGAEVAVTCTVFQTQPVTSQPQPE-GANEAVPTPVVDPDAPPSPPLGAPGLPPAGSP PDSHVLLAAPPGHQLHR$_{311}$ (SEQ ID NO: 2), or a variant thereof.

According to another embodiment, the fragment of Fetuin-A is a polypeptide comprising or consisting of the following sequence: $_{255}$VTSQP$_{259}$ (SEQ ID NO: 3), or a variant thereof.

According to a further embodiment, the fragment of Fetuin-A is a polypeptide comprising or consisting of the following sequence: $_{268}$VPTPV$_{272}$ (SEQ ID NO: 4), or a variant thereof.

The "O-linked oligosaccharide chain bearing two terminal sialic acid residues" preferably comprises a mucin-type O-glycosylation, which herein refers to a glycan attached via O-linked N-acetylgalactosamine (GalNAc) to a threonine or serine residue. More preferably, the "O-linked oligosaccharide chain bearing two terminal sialic acid residues" comprises a glycan comprising an O-linked N-acetylgalactosamine (GalNAc), linked to a galactose (Gal), the N-acetylgalactosamine (GalNAc) and the galactose (Gal) being both sialylated, each with one N-acetylneuraminic acid (Neu5Ac or NeuAc) (see FIG. 4 and Table 2).

The "O-linked oligosaccharide chain bearing one terminal sialic acid residue" preferably comprises a mucin-type O-glycosylation, which herein refers to a glycan attached via O-linked N-acetylgalactosamine (GalNAc) to a threonine or serine residue. More preferably, the "O-linked oligosaccharide chain bearing one terminal sialic acid residue" comprises a glycan comprising an O-linked N-acetylgalactosamine (GalNAc), linked to a galactose (Gal), the galactose (Gal) being sialylated with one N-acetylneuraminic acid (Neu5Ac or NeuAc) (see FIG. 4 and Table 2).

The presence of post-translational modifications on purified proteins may be determined by nanoLC-MS/MS, as described in Example 1. Typically, purified Fetuin A or asialo-Fetuin A proteins may be solubilized in a buffer containing 8 M urea, 75 mM Tris pH 8.5 and 5 mM TCEP. Proteins may then be alkylated with iodoacetamide (10 mM) for 20 min and subjected to a trypsin digestion in-solution (protein/protease mass ratio 50/1) for 3 h at 37° C. in presence of 0.018% of ProteaseMax surfactant (Promega, Charbonnieres, France). 2.5% FA may for instance be added to the mixture to quench enzymatic activity and peptides may be stored at −80° C. until the day of analysis. Typically, peptide samples may then be spun at 18000 g and the peptide mixture may be separated using a $C_{18}$ column (Acclaim® PepMap RSLC 75 μm ID, 25 cm, 2 μm particles, and pore size at 100 Å, Thermo Scientific). N- and O-glycopeptides may for instance be manually identified by the presence of glycan-specific oxonium ion fragments.

The 'biological sample' may be, without limitation, blood, plasma, serum, nasal secretion, saliva, bronchoalveolar fluid, cerebrospinal fluid or urine. The sample is preferably taken before the commencement of therapy or before the planned commencement of therapy. The sample may also be taken after the commencement of therapy, for example after one round of therapy is completed in order to decide whether to proceed to further rounds. Where the method is a method of determining efficacy of therapy, the sample is preferably taken before and/or after the commencement of therapy.

Detection of the 'level of expression' of a Fetuin-A polypeptide may refer to the level of expression of any individual isoform or variant of said polypeptide; the collective level of expression of selected isoforms or variants of said polypeptide; or the total level of expression of said polypeptide including the reference sequence and all isoforms and variants. For example, detection of the level of expression of a Fetuin-A polypeptide comprising an O-linked oligosaccharide chain bearing two terminal sialic acid residues at position 256 may include detection of the level of expression of a particular glycoform comprising an O-linked oligosaccharide chain bearing two terminal sialic acid residues at position 256, a subset of glycoforms comprising an O-linked oligosaccharide chain bearing two terminal sialic acid residues at position 256, all glycoforms comprising an O-linked oligosaccharide chain bearing two terminal sialic acid residues at position 256, or all forms of Fetuin-A whether modified or unmodified, provided they comprise an O-linked oligosaccharide chain bearing two terminal sialic acid residues at position 256.

In some embodiments, the methods of the invention involve detection of a single protein isoform. In other embodiments, more than one protein isoform is detected, for example at least 2, 3, 4, 5, 6, 7, 8, 9, 10, 11, 12, 13, 14 or at least 15 protein isoforms.

In an embodiment, the level of expression of the Fetuin-A polypeptide or fragment thereof comprising:
a) an O-linked oligosaccharide chain bearing two terminal sialic acid residues at position 256; or
b) an O-linked oligosaccharide chain bearing two terminal sialic acid residues at position 256 and an O-linked oligosaccharide chain bearing two terminal sialic acid residues at position 270, by reference to the amino acid positions as shown in sequence SEQ ID NO: 1;
is determined.

In another embodiment, the level of expression of the Fetuin-A polypeptide or fragment thereof comprising an O-linked oligosaccharide chain bearing two terminal sialic acid residues at position 270, by reference to the amino acid positions as shown in sequence SEQ ID NO: 1;
is determined.

In a further embodiment, the level of expression of the Fetuin-A polypeptide or fragment thereof comprising an O-linked oligosaccharide chain bearing two terminal sialic acid residues at position 270 and an O-linked oligosaccharide chain bearing one terminal sialic acid residue at position 256, by reference to the amino acid positions as shown in sequence SEQ ID NO: 1;
is determined.

Control

The expression of the Fetuin-A polypeptide or fragment thereof comprising (i) an O-linked oligosaccharide chain bearing two terminal sialic acid residues at position 256, (ii) an O-linked oligosaccharide chain bearing two terminal sialic acid residues at position 270, (iii) an O-linked oligosaccharide chain bearing two terminal sialic acid residues at position 256 and an O-linked oligosaccharide chain bearing two terminal sialic acid residues at position 270, and/or (iv) an O-linked oligosaccharide chain bearing one terminal sialic acid residue at position 256 and an O-linked oligosaccharide chain bearing two terminal sialic acid residues at position 270, by reference to the amino acid positions as shown in sequence SEQ ID NO: 1, in the patient sample may be compared with a control standard value and/or with the expression of said polypeptide or fragment in a control sample.

A control standard value may be an absolute value, such as the polypeptide or fragment thereof total abundance per volume of biological sample. A control standard value may also be measured as the ratio of said polypeptide or fragment thereof on any polypeptide or fragment thereof, or on the sum of part or all polypeptide or fragment thereof in a biological sample. More preferably a control standard value may be the relative abundance of a fragment of the Fetuin-A polypeptide, such as SEQ ID NO:2, SEQ ID NO:3 or SEQ ID NO:4, compared to the total peptide abundance of a biological sample. The biological sample may be depleted or not in specific proteins prior to measurement. Preferably the sample is depleted in Albumin, IgG, anti-trypsin (or α1-antitrypsin), IgA, transferrin and haptoglobulin. More preferably the sample is depleted in any of the following proteins Albumin, IgG, anti-trypsin (or α1-antitrypsin), IgA, transferrin and haptoglobulin, α1-acid glycoprotein, α2-macroglobulin, apolipoprotein A1, apolipoprotein A2, complement C3, fibrinogen, IgM and transthyretin or a combination thereof.

The control sample may be that of a control subject or subjects. The control subject may be, for example, a subject previously identified as a non-responder or poor responder to therapy, or a group of such subjects. Alternatively, the control subject may be a subject previously identified as a responder to therapy, or a group of such subjects. The control sample may also be obtained from a group of subjects selected at random. The control may also comprise an internal control. For example, a subset of a group of candidates for therapy may be selected for therapy by comparing the level of expression of a Fetuin-A polypeptide or fragment thereof in all candidates and selecting those candidates with the highest level of expression for therapy. A standard value may be obtained by, for example, detecting the level of expression in a group of subjects and obtaining an average or median figure.

As will be clear to the skilled person, the nature of the comparison of the patient sample with the control and the conclusions drawn will depend on the nature of the control. The inventors have shown that Fetuin-A polypeptides or fragments thereof, bearing specific post-translational modifications are up-regulated in responder subjects. In this context, where the control is based on a non-responder subject or group of such subjects, a value the same as or similar to, or lower than, the control may be indicative of non-responsiveness to therapy, whereas a value higher than the control may be indicative of responsiveness to therapy. Conversely, where the control is based on a responder subject or group of such subjects, a value the same as or similar to, or higher than, the control may be indicative of responsiveness to therapy, whereas a value lower than the control may be indicative of non-responsiveness to therapy. Where the control is based on an average or median value obtained from a random group of subjects, a value the same as or similar to or higher than the control may be indicative of responsiveness to therapy.

Accordingly, identifying a patient as likely to be a responder or non-responder to immunotherapy based on the comparison with the control can be performed by:

(i) determining that the patient is likely to be a responder to immunotherapy if the control is derived from a responder subject or group of responder subjects known to respond to said immunotherapy, and if a level of expression of said Fetuin-A polypeptide, or fragment thereof, in the patient sample is equal to or greater than the level of expression in the control; or (ii) determining that the patient is likely to be a responder to immunotherapy if the control is derived from a non-responder subject or group of non-responder subjects, and if the level of expression of said Fetuin-A polypeptide, or fragment thereof, in the patient sample is greater than the level of expression in the control; or (iii) determining that the patient is likely to be a responder to immunotherapy if the control is derived from a randomly selected group of subjects, and if a level of expression of said Fetuin-A polypeptide, or fragment thereof, in the patient sample is equal to or greater than the level of expression in the control.

Also, selecting or rejecting said patient for immunotherapy based on the comparison with the control is performed by:

(i) if the control is derived from a responder subject or group of responder subjects known to respond to said immunotherapy, selecting the patient for immunotherapy if the level of expression of said Fetuin-A polypeptide, or fragment thereof, in the patient sample is equal to or greater than the level of expression in the control (and rejecting the patient from immunotherapy if the level of expression of said Fetuin-A polypeptide, or fragment thereof, in the patient sample is lower than the level of expression in the control);

(ii) if the control is derived from a non-responder subject or group of non-responder subjects, selecting the patient for immunotherapy if the level of expression of said Fetuin-A polypeptide, or fragment thereof, in the patient sample is greater than the level of expression in the control (and rejecting the patient from immunotherapy if the level of expression of said Fetuin-A polypeptide, or fragment thereof, in the patient sample is lower than the level of expression in the control); or (iii) if the control is derived from a randomly selected group of subjects, selecting the patient for immunotherapy if the level of expression of said Fetuin-A polypeptide, or fragment thereof, in the patient sample is equal to or greater than the level of expression in the control (and rejecting the patient from immunotherapy if the level of expression of said Fetuin-A polypeptide, or fragment thereof, in the patient sample is lower than the level of expression in the control).

An increase or decrease in the level of expression of protein polypeptide, variants thereof and fragments thereof, may be detected in a patient sample compared to a control, as detailed above. The fold change in the patient sample compared to the control may be at least 1.1, at least 1.2, at least 1.4, at least 1.6, at least 1.8, at least 2, at least 2.2, at least 2.4, at least 2.6, at least 2.8, at least 3, at least 3.5, at least 4, at least 4.5, at least 5, at least 6, at least 7 or at least 8-fold.

Moreover, the control standard value or the level of expression of said polypeptide or fragment thereof in a control sample may vary depending on the distinction between responder and non-responder patient, this distinction being determined on the basis of the threshold selected for clinical efficacy. For example, the control standard value or the level of expression of said polypeptide or fragment may be determined on the basis of a threshold for clinical efficacy in which administration of the treatment results in an improvement of clinical symptoms. More particularly, this may be determined on the basis of an improvement of clinical symptoms detected by a reduction of at least 5%, at least 10%, at least 15%, at least 20%, at least 30%, at least 40% or at least 50% of at least one symptom or a combination of symptoms, as further illustrated below.

The control standard value may also be determined on the basis of an absolute value. As will be clear to the skilled person, the absolute value will be depending on the assay used. The absolute value can be determined as the threshold value of the abundance of Fetuin-A polypeptide or a fragment thereof comprising (i) an O-linked oligosaccharide chain bearing two terminal sialic acid residues at position 256, (ii) an O-linked oligosaccharide chain bearing two terminal sialic acid residues at position 270, (iii) an O-linked oligosaccharide chain bearing two terminal sialic acid residues at position 256 and an O-linked oligosaccharide chain bearing two terminal sialic acid residues at position 270, and/or (iv) an O-linked oligosaccharide chain bearing one terminal sialic acid residue at position 256 and an O-linked oligosaccharide chain bearing two terminal sialic acid residues at position 270, by reference to the amino acid positions as shown in sequence SEQ ID NO: 1, in a representative sample of patient for which immunotherapy resulted in an improvement of clinical symptoms detected by a reduction of at least 5%, at least 10%, at least 15%, at least 20%, at least 30%, at least 40% or at least 50% of at least one symptom or a combination of symptoms, as further illustrated below.

In a preferred embodiment, the control standard value consists of a relative abundance of SEQ ID NO:2, comprising an O-linked oligosaccharide chain bearing two terminal sialic acid residues at position 256 and an O-linked oligosaccharide chain bearing two terminal sialic acid residues at position 270, of at least 0.0046%, 0.0133%, at least 0.0219%, at least 0.0393%, at least 0.0566% or at least 0.0740% of the total peptide abundance in a biological sample. The control standard value may also be expressed as a relative abundance of SEQ ID NO:2, comprising an O-linked oligosaccharide chain bearing two terminal sialic acid residues at position 256 and an O-linked oligosaccharide chain bearing two terminal sialic acid residues at position 270, of at least 3,600, at least 10,400, at least 17,100, at least 30,600, at least 44,100 or at least 57,600, units in a biological sample. Moreover, the control standard value expressed as a relative abundance of said peptide in units in a biological sample may also be established by (i) defining a threshold value for the percentage of ARTSS improvement, and (ii) determining the unit value by applying the equation $Y=0.0007397*X+7.337$ where Y="threshold value for the percentage of ARTSS improvement" and X="Unit Value". Likewise, the control value expressed as a ratio of the relative abundance of said peptide with the total peptide abundance in a biological sample may further be established by (i) defining a threshold value for the percentage of ARTSS improvement, (ii) determining the unit value by applying the equation $Y=0.0007397*X+7.337$ where Y="threshold value for the percentage of ARTSS improvement" and X="Unit Value", and (iii) determining the ratio of the relative abundance of said peptide with the total peptide abundance in a biological sample by dividing the Unit Value determined in step (ii) by the number 778009.62 which corresponds to the hundredth of the mean of total peptide abundance. More preferably, the above control standard values are applicable for a method where a serum sample is being depleted of main serum sample proteins such as Albumin, IgG, anti-trypsin, IgA, transferrin and haptoglobulin, then digested, more preferably 50 μg of depleted serum protein digested with trypsin at an enzyme/substrate ratio of at least 1/25, and then abundance is measured by mass spectrometry, more preferably label free mass spectrometry with peptide detection performed with peptide intensity>1000, peptide abundance>2000 and 2+≤peptide charge≤12+.

In another preferred embodiment, the control standard value consists of a relative abundance of SEQ ID NO:2, comprising an O-linked oligosaccharide chain bearing one terminal sialic acid residues at position 256 and an O-linked oligosaccharide chain bearing two terminal sialic acid residues at position 270, of at least 0.0200%, at least 0.0547%, at least 0.0894%, at least 0.1588%, at least 0.2282% or at least 0.2976% of the total peptide abundance in a biological sample. The control standard value may also be expressed as a relative abundance of SEQ ID NO:2, comprising an O-linked oligosaccharide chain bearing one terminal sialic acid residue at position 256 and an O-linked oligosaccharide chain bearing two terminal sialic acid residues at position 270, of at least 15,600, at least 42,600, at least 69,600, at least 123,600, at least 117,600 or at least 231,600 units in a biological sample. Moreover, the control standard value expressed as a relative abundance of said peptide in units in a biological sample may also be established by (i) defining a threshold value for the percentage of ARTSS improvement, and (ii) determining the unit value by applying the equation Y=0.0001852*X+7.111 where Y="threshold value for the percentage of ARTSS improvement" and X="Unit Value". Likewise, the control value expressed as a ratio of the relative abundance of said peptide with the total peptide abundance in a biological sample may further be established by (i) defining a threshold value for the percentage of ARTSS improvement, (ii) determining the unit value by applying the equation Y=0.0007397*X+7.337 where Y="threshold value for the percentage of ARTSS improvement" and X="Unit Value", and (iii) determining the ratio of the relative abundance of said peptide with the total peptide abundance in a biological sample by dividing the Unit Value determined in step (ii) by the number 778009.62 which corresponds to the hundredth of the mean of total peptide abundance. More preferably, the above control standard values are applicable for a method where a serum sample is being depleted of main serum sample proteins such as Albumin, IgG, anti-trypsin, IgA, transferrin and haptoglobulin, then digested, more preferably 50 μg of depleted serum protein digested with trypsin at an enzyme/substrate ratio of at least 1/25, and then abundance is measured by mass spectrometry, more preferably label free mass spectrometry with peptide detection performed with peptide intensity>1000, peptide abundance>2000 and 2+≤peptide charge≤12+.

In an additional preferred embodiment, the control standard value consists of a relative abundance of SEQ ID NO:2, comprising an O-linked oligosaccharide chain bearing two terminal sialic acid residues at position 256 and an O-linked oligosaccharide chain bearing two terminal sialic acid residues at position 270, expressed in units in a biological sample, which is established by (i) defining a threshold value for the percentage of ARTSS improvements, (ii) defining a threshold value of sensitivity of the test and (iii) determining the corresponding unit value. Alternatively, instead of determining a threshold value of sensitivity of the test in step (ii), a threshold value of specificity may be selected. Likewise, the control value expressed as a ratio of the relative abundance of said peptide with the total peptide abundance in a biological sample may further be established by (i) defining a threshold value for the percentage of ARTSS improvement, (ii) defining a threshold value of sensitivity of the test, (iii) determining the corresponding unit value and (iv) determining the ratio of the relative abundance of said peptide with the total peptide abundance in a biological sample by dividing the Unit Value determined in step (iii) by the number 778009.62 which corresponds to the hundredth of the mean of total peptide abundance. Alternatively, instead of determining a threshold value of sensitivity of the test in step (ii), a threshold value of specificity may be selected. As a more preferred embodiment, any of the value units in a biological sample defined in tables 3, 4 and 5 can be selected. More preferably, the above control standard values are applicable for a method where a serum sample is being depleted of main serum sample proteins such as Albumin, IgG, anti-trypsin, IgA, transferrin and haptoglobulin, then digested, more preferably 50 μg of depleted serum protein digested with trypsin at an enzyme/substrate ratio of at least 1/25, and then abundance is measured by mass spectrometry, more preferably label free mass spectrometry with peptide detection performed with peptide intensity>1000, peptide abundance>2000 and 2+≤peptide charge≤12+.

Detection of Proteins or Fragment Thereof

The level of expression of the Fetuin-A polypeptide or fragment comprising (i) an O-linked oligosaccharide chain bearing two terminal sialic acid residues at position 256, (ii) an O-linked oligosaccharide chain bearing two terminal sialic acid residues at position 270, (iii) an O-linked oligosaccharide chain bearing two terminal sialic acid residues at position 256 and an O-linked oligosaccharide chain bearing two terminal sialic acid residues at position 270, and/or (iv) an O-linked oligosaccharide chain bearing one terminal sialic acid residue at position 256 and an O-linked oligosaccharide chain bearing two terminal sialic acid residues at position 270, may be determined by gel electrophoresis (SDS-PAGE), by mass analysis, by affinity assay such as assays based on lectin or aptamer, by immuno-assay, or any combination thereof.

Polypeptide expression may be determined by mass analysis, such as mass spectrometry (MS). Qualitative and quantitative mass spectrometric techniques are known and used in the art. A quantitative LC-MS/MS can also be used.

The level of expression of the Fetuin-A polypeptide or fragment thereof comprising (i) an O-linked oligosaccharide chain bearing two terminal sialic acid residues at position 256, (ii) an O-linked oligosaccharide chain bearing two terminal sialic acid residues at position 270, (iii) an O-linked oligosaccharide chain bearing two terminal sialic acid residues at position 256 and an O-linked oligosaccharide chain bearing two terminal sialic acid residues at position 270, and/or (iv) an O-linked oligosaccharide chain bearing one terminal sialic acid residue at position 256 and an O-linked oligosaccharide chain bearing two terminal sialic acid residues at position 270, may for instance be determined by quantification of the absolute amount of said Fetuin-A polypeptide or fragment in a biological sample by:

a) providing a known amount of the Fetuin-A polypeptide or fragment thereof, optionally labelled, as a calibration standard, b) degrading the sample to obtain a mixture of polypeptides, optionally labelled, wherein at least the polypeptides in the degraded sample or in the calibration standard are labelled, and if both polypeptides are labelled, the labelling agent used for the polypeptides in the calibration standard is different from the labelling agent used for the polypeptides in the degraded sample, c) quantifying the absolute amount of the polypeptide according to the invention in the degraded sample by correlating the amount of the polypeptide in the calibration standard with the amount of the corresponding polypeptide in the degraded sample by mass analysis.

The quantification step may for instance be performed using mass spectrometry, labelling may for example be performed using ITRAQ™ chemistry, and the degradation step may for instance be performed by using a proteolytic enzyme, such as trypsin, papain, pepsin, ArgC, LysC, V8 protease, AspN, pronase, chymotrypsin and carboxypeptidase C, or a combination thereof, as described in WO 2007/031080.

The quantification of the amount of said Fetuin-A polypeptide or fragment thereof may also be determined by quantification of its relative abundance.

This may be determined by:

a) degrading with pronase the sample containing the polypeptide to be quantified to obtain a mixture of polypeptides, b) quantifying the relative abundance of the polypeptide according to the invention in the pronase-digested sample by measuring the relative abundance of the peptide of SEQ ID NO:3 comprising an O-linked oligosaccharide chain bearing two terminal sialic acid residues at position 256 and/or by measuring the relative abundance of the peptide of SEQ ID NO:4 comprising an O-linked oligosaccharide chain bearing two terminal sialic acid resides at position 270.

In Huang et al. 2014, an m/z value of 594.2537 for z=2 was provided for the peptide of SEQ ID NO:3 comprising an O-linked oligosaccharide chain bearing two terminal sialic acid residues at position 256, and an m/z value of 730.3203 for z=2 was provided for the peptide of SEQ ID NO:4 comprising an O-linked oligosaccharide chain bearing two terminal sialic acid residues at position 270.

Preferably, the quantification of the amount of said Fetuin-A polypeptide or fragment thereof may be determined by:

a) degrading with trypsin the sample containing the polypeptide to be quantified to obtain a mixture of polypeptides b) quantifying the relative abundance of the polypeptide according to the invention in the trypsin-digested sample by measuring the relative abundance of the peptide of SEQ ID NO:2 comprising an O-linked oligosaccharide chain bearing two terminal sialic acid residues at position 256 and an O-linked oligosaccharide chain bearing two terminal sialic acid residues at position 270, and/or by measuring the relative abundance of the peptide of SEQ ID NO:2 comprising an O-linked oligosaccharide chain bearing one terminal sialic acid residue at position 256 and an O-linked oligosaccharide chain bearing two terminal sialic acid residues at position 270.

More preferably, the quantification of the amount of said Fetuin-A polypeptide or fragment thereof may be determined by:

a) Providing a serum sample depleted in albumin, IgG, anti-trypsin, IgA, transferrin and haptoglobulin b) degrading the depleted serum sample with trypsin, preferably with a ratio of enzyme to the depleted serum sample of at least 1:25 weight/weight, to obtain a mixture of polypeptides, c) quantifying the relative abundance of the polypeptide according to the invention in the trypsin-digested depleted serum sample by measuring the relative abundance of the peptide of SEQ ID NO:2 comprising an O-linked oligosaccharide chain bearing two terminal sialic acid residues at position 256 and an O-linked oligosaccharide chain bearing two terminal sialic acid residues at position 270, and/or by measuring the relative abundance of the peptide of SEQ ID NO:2 comprising an O-linked oligosaccharide chain bearing one terminal sialic acid residue at position 256 and an O-linked oligosaccharide chain bearing two terminal sialic acid residues at position 270, with peptide detection performed with peptide intensity>1000, peptide abundance>2000 and 2+≤peptide charge≤12+

For said quantification, it is preferred that the depleted serum sample submitted to trypsin digestion comprises at least 50 µg of total protein.

In the present application, an m/z value of 1858.2795 for z=5 is described the peptide of SEQ ID NO:2 comprising an O-linked oligosaccharide chain bearing two terminal sialic acid residues at position 256 and an O-linked oligosaccharide chain bearing two terminal sialic acid residues at position 270, and an m/z value of 1800.0704 for z=5 is described the peptide of SEQ ID NO:2 comprising an O-linked oligosaccharide chain bearing one terminal sialic acid residue at position 256 and an O-linked oligosaccharide chain bearing two terminal sialic acid residues at position 270.

The calibration peptide is preferably prepared by peptide synthesis. The number of amino acids in the calibration standard peptide is preferably in the range of 2-20 amino acids, more preferably in the range of 4-15 and most preferred in the range of 6-15. The number is dependent on the optimal enzymatic cleavage site found to match to the amino acid sequence within the sample i.e. the constant or the variable region sequence when the sample is cleaved by an enzyme. Furthermore, the calibration standard peptide to be used depends on the label and the quantification method to be used in order to give a detectable signal and fragmentation when analysed in a MS instrument.

In a specific embodiment, the polypeptide of sequence SEQ ID NO: 1, the polypeptide of sequence SEQ ID NO: 2, the polypeptide of sequence SEQ ID NO: 3 or the polypeptide of sequence SEQ ID NO: 4, optionally labeled with one or more mass-modifying labeling agent, is used as a calibration standard protein. More specifically, the polypeptide of sequence SEQ ID NO: 1 or the polypeptide of SEQ ID NO:2 comprise an O-linked oligosaccharide chain bearing two terminal sialic acid residues at position 256 and an O-linked oligosaccharide chain bearing two terminal sialic acid residues at position 270, by reference to the amino acid positions as shown in sequence SEQ ID NO: 1.

Expression may also be determined using an antibody which binds specifically to a Fetuin-A polypeptide or fragment comprising an O-linked oligosaccharide chain bearing two terminal sialic acid residues at position 256, an O-linked oligosaccharide chain bearing two terminal sialic acid residues at position 270, an O-linked oligosaccharide chain bearing two terminal sialic acid residues at position 256 and an O-linked oligosaccharide chain bearing two terminal sialic acid residues at position 270, and/or an O-linked oligosaccharide chain bearing one terminal sialic acid residue at position 256 and an O-linked oligosaccharide chain bearing two terminal sialic acid residues at position 270.

As used herein the terms "antibody" and "immunoglobulin" have the same meaning and are used in the broadest sense and specifically covers intact monoclonal antibodies, polyclonal antibodies, chimeric, antibodies, diabodies, multispecific antibodies (e.g. bispecific antibodies) formed from at least two intact antibodies, and also antibody fragments.

In particular, the antibody of the invention may be comprised in an anti-serum.

The invention pertains in particular to an antibody directed against the sequence SEQ ID NO: 2 comprising an O-linked oligosaccharide chain bearing two terminal sialic acid residues at position 256 and an O-linked oligosaccharide chain bearing two terminal sialic acid residues at position 270, against the sequence SEQ ID NO: 2 comprising an O-linked oligosaccharide chain bearing one terminal sialic acid residue at position 256 and an O-linked oligosaccharide chain bearing two terminal sialic acid residues at position 270, against the sequence SEQ ID NO: 3 comprising an O-linked oligosaccharide chain bearing two terminal sialic acid residues at position 256 or against the sequence SEQ ID NO: 4 comprising an O-linked oligosaccharide chain bearing two terminal sialic acid residues at position 270.

The term "monoclonal antibody" or "mAb" as used herein refers to an antibody molecule of a single amino acid composition, that is directed against a specific antigen and which may be produced by a single clone of B cells or hybridoma. Monoclonal antibodies may also be recombinant, i.e. obtained by protein engineering. Recombinant antibodies may be produced in a mammalian cell line such as CHO, NSO, PERC6 or any other cell after transfection.

The term "polyclonal antibodies" refers to a combination of immunoglobulins directed against a specific antigen, each immunoglobulin possibly binding to a different epitope on the antigen. Polyclonal antibodies are generally produced by immunisation of a suitable mammal, such as a mouse, rabbit or goat.

The term "chimeric antibody" refers to an engineered antibody which comprises a VH domain and a VL domain of an antibody derived from a non-human animal, in association with a CH domain and a CL domain of another antibody, in particular a human antibody. The non-human animal may be a mouse, a rat, a hamster, a rabbit or the like.

The expression "bispecific antibody" refers to an engineered antibody possessing two different antigen binding sites. In a preferred embodiment of the invention, the at least one CD5 binding molecule and at least one HLA-DR binding molecule of the invention is a bispecific antibody which is able to bind to CD5 and to HLA-DR.

The term "diabodies" refers to small antibody fragments with two antigen-binding sites, which fragments comprise a heavy-chain variable domain (VH) connected to a light-chain variable domain (VL) in the same polypeptide chain (VH-VL). In general, by using a linker that is too short to allow pairing between the two domains on the same chain, the domains are forced to pair with the complementary domains of another chain and create two antigen-binding sites. Preferably the diabody is able to recognize CD5 and HLA-DR.

The expression "antibody fragments" comprise a portion of an intact antibody, preferably the antigen binding or variable region of the intact antibody. Examples of antibody fragments include Fv, Fab, F(ab')2, Fab', dsFv, scFv, sc(Fv)2, diabodies and multispecific antibodies formed from antibody fragments.

The antibody may be immobilized on a solid support. Antibodies may be used to determine protein expression in a range of immunological assays including competitive and non-competitive assay systems using techniques such as Western blotting, radioimmunoassay such as RIA (radio-linked immunoassay), ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, e.g. FIA (fluorescence-linked immunoassay), chemiluminescence immunoassays, electro-chemiluminescence immunoassay (ECLIA) and protein A immunoassays. Such assays are routine and well known to the person skilled in the art.

Expression may alternatively be determined using a protein-specific aptamer. An aptamer is a short peptide capable of specifically binding to a specific protein sequence, consisting of a variable peptide loop attached at both ends to a protein scaffold. Methods for making protein aptamers are well known in the art, the most commonly used method being the yeast two-hybrid system. Such aptamers may preferably be labeled in order to allow the detection of a protein-ligand interaction. A nanotechnology-based assay could also be used.

As used herein, a lectin refers to a carbohydrate-binding protein or polypeptide, or a protein or polypeptide highly specific for sugar moieties. More preferably, lectins are glycan-binding proteins that bind to their target glycan moiety with high specificity. As such, lectins are used for protein-carbohydrate recognition and to detect subtle variations in carbohydrate structures. Lectins are also shown to be sensitive to changes in protein glycosylations, such as changes in the content of sialic acid or fucosyl residues present in the serum glycoproteins. Examples of lectins and their glycan specificities are listed below (see Fanavan et al., *Electrophoresis*, July 2012, 33(12):1746-54):

TABLE 1

| Lectin | Specificity |
| --- | --- |
| Concanavalin A (Con A) | High-mannose type, branched-mannosidic structures |
| Wheat germ agglutinin (WGA) | N-acetylglucosamine; chitobiose |
| Jacalin (JAC) | Galactosyl (b-1,3) N-acetylgalactosamine (O-glycoproteins) |
| *Sambucus nigra* lectin (SNA, EBL) | Sialic acid attached to terminal galactose in (a-2,6) |
| Peanut agglutinin (PNA) | Galactosyl (b-1,3) N-acetylgalactosamine (T-Antigen) |
| *Lens culinaris* agglutinin (LCA) | Linked mannose residues |
| *Phaseolus vulgaris* leucoagglutinin (PHA-L) | Tri/tetra-antennary complex-type N-glycan |
| *Aleuria aurantia* lectin (AAL) | Fucose linked (a-1,6) to N-acetylglucosamine; fucose linked (a-1,3) to N-acetyllactosamine |

In an embodiment, the antibody, aptamer or lectin binds specifically to an O-linked oligosaccharide chain bearing one or two terminal sialic acid residue(s) at position 256, or to an O-linked oligosaccharide chain bearing two terminal sialic acid residues at position 270; or the antibody, aptamer or lectin does not bind significantly to Fetuin-A polypeptide or fragment thereof lacking an O-linked oligosaccharide chain bearing one or two terminal sialic acid residue(s) at position 256 and/or an O-linked oligosaccharide chain bearing two terminal sialic acid residues at position 270.

Therapeutic Applications

'Allergy' or 'type 1 hypersensitivity' is a condition characterized by production of allergen-specific IgE in response to a specific allergen, usually a protein. Clinical manifestations and symptoms of allergy may include nasal congestion, nasal pruritis, ocular pruritis, tearing, rhinorrhoea, sinusitis, rhinitis, sneezing, wheezing, conjunctivitis, dermal itching, dermatitis, skin irritation, vomiting, stomach cramps, indigestion, diarrhea, hives, shortness of breath, repetitive cough, trouble swallowing, swelling of the tongue and/or lips, weak pulse, dizziness or confusion and asthma.

An 'allergen' is a substance, usually a protein, which elicits the production of IgE antibodies in predisposed individuals. Allergens may include pollen allergens (such as tree, herb, weed and grass pollen allergens), insect allergens (such as inhalant, saliva and venom allergens, e.g. cockroach, midge and house dust mite allergens and hymenoptera venom allergens), animal hair and dander allergens (from e.g. dog, cat, horse, rat, mouse, rabbit) and food allergens (such as peanut, tree nut, milk, egg, wheat, seafood).

Preferably, the allergen(s) administered to the patient suffering from allergy, as immunotherapy, correspond(s) to the allergen(s) to which the patient is allergic.

In a preferred embodiment, the patient has house dust mite allergy and the immunotherapy uses house dust mite extract from one or more of *Dermatophagoides pteronyssinus* and *Dermatophagoides farinae*. In a specific embodiment, the immunotherapy comprises administration of extract from one or more of *Dermatophagoides pteronyssinus* and *Dermatophagoides farinae*.

In another preferred embodiment, the patient has grass pollen allergy and the immunotherapy uses grass pollen allergen. In a specific embodiment, the immunotherapy comprises administration of 5-grass-pollen extract(s), in particular of extract(s) from pollen of one or more of *Dactylis, Poa, Lolium, Anthoxanthum* and *Phleum* genera.

For instance, a protein allergen may be selected from the group consisting of a protein allergen of the genus *Dermatophagoides*; a protein allergen of the genus *Fells*; a protein allergen of the genus *Ambrosia*; a protein allergen of the genus *Lolium*; a protein allergen of the genus *Cryptomeria*; a protein allergen of the genus *Alternaria*; a protein allergen of the genus *Alder*, a protein allergen of the genus *Betula*; a protein allergen of the genus of *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus *Canine*; a protein allergen of the genus *Blattella*; a protein allergen of the genus *Apis*; a protein allergen of the genus *Cupressus*; a protein allergen of the genus *Thuya*; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Juniperus*; a protein allergen of the genus *Dactylis*; a protein allergen of the genus *Festuca*; a protein allergen of the genus *Poa*; a protein allergen of the genus *Lolium*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; a protein allergen of the genus *Sorghum*; a protein allergen of the genus *Arachis*; a protein allergen of the genus *Gallus* and a protein allergen of the genus *Bos*.

Examples of various known protein allergens derived from some of the above-identified genus include: *Betula* (*verrucosa*) Bet v 1; Bet v 2; *Blomia* Blo t 1; Blo t 3; Blo t 5; Blo t 12; *Cynodon* Cyn d 1; *Dermatophagoides* (*pteronyssinus* or *farinae*) Der p 1; Der p 2; Der p 3; Der p 7; Der f 1; Der f 2; Der f 3; Der f 7; *Felis* (*domesticus*) Fel d 1; *Ambrosia* (*artemiisfolia*) Amb a 1; Amb a 3; Amb a 4; Amb a 5; Amb a 6; Amb a 7; Amb a 8; Amb a 9; Amb a 10; Amb a 11; *Lolium* (*perenne*) Lol p 1; Lot p 2; Lol p 3; Lot p 4; Lol p 9 (Lol p 5 or Lol p 1b); *Cryptomeria* (*japonica*) Cry j 1; Cry j 2; *Canis* (*familiaris*) Can f 1; Can f 2; *Juniperus* (*sabinoides* or *virginiana*) Jun s 1; Jun v 1; *Juniperus* (*ashei*) Jun a 1; Jun a 2; *Dactylis* (*glomerata*) Dae g 1; Dae g 5; *Poa* (*pratensis*) Poa p 1; *Phleum* (*pratense*) Phl p 1; Phl p 5; Phl p 6; *Sorghum* (*halepensis*) Sor h 1; *Arachis* (*hypogaea*) Ara h 1; Ara h 2; Ara h 6; *Gallus* (*domesticus*) Gal d 1; Gal d 2; Gal d 3; Gal d 4; and *Bos* (*domesticus*) Bos d 2; Bos d 3; Bos d 4; Bos d 5; Bos d 6; Bos d 7; Bos d 8; Bos d 9; Bos d 10; Bos d 11; Bos d 12.

As used herein an "auto-antigen" refers to an endogenous antigen capable of stimulating the production of auto-antibodies, for instance in an auto-immune reaction.

In autoimmune disorders, the immune system produces antibodies to an endogenous antigen. Antibody-coated cells, like any similarly coated foreign particle, activate the complement system, resulting in tissue injury. Most human autoimmune disorders are specific antigen-driven T-cell diseases. T-cell clones responding to specific antigenic epitopes are responsible for the initiation and/or the propagation of these diseases. Similarly, specific antigen-driven T-cell responses are responsible for the rejection of organ allografts. Activated T cells provide the "engine" for the chronic inflammation that is associated with autoimmune disorders. Autoimmune disorders include but are not limited to rheumatoid arthritis (RA), multiple sclerosis (MS), inflammatory bowel disease (IBD), systemic lupus erythematodes (SLE), Graves' disease and diabetes mellitus.

'Immunotherapy' refers to the administration of an allergen or autoantigen to a patient with the aim of reducing current or future immune response, such as an IgE response, and/or manifestation of clinical symptoms of allergy or an autoimmune disorder. Immunotherapy is conventionally carried out by administering repeatedly a monodose or incremental doses of an allergen to a patient in need thereof, thereby resulting in an adaptive immune response of the patient who becomes desensitised to the allergen.

Immunotherapy may comprise administration of allergen to a mucosal surface, optionally a sublingual, oral, buccal, ocular, rectal, urinal, pulmonal or ear surface. In particular, immunotherapy may be sublingual immunotherapy. Alternatively, immunotherapy may comprise administration via a parenteral route, such as subcutaneously or intravenously, for example via injection, or via alternative routes such as intranasal, skin immunisation e.g; transdermal or epicutaneous, or intralymphatic administration.

The allergen used for immunotherapy may be a single allergenic substance or a mixture of such substances, for example a mixture of proteins. It may be a partially or fully purified allergen extract, such as a pollen extract, a house dust mite extract, a natural purified protein, a recombinant protein, a hypoallergen or allergoid or peptide derived therefrom, or any chemically synthesised peptide or polypeptide bearing the same primary sequence. For example, where the immunotherapy is used to treat grass pollen allergy, the allergen administered for immunotherapy may be a grass pollen extract from pollen of one or several genera of grasses, such as *Dactylis, Poa, Lolium, Anthoxanthum* and *Phleum* genera. Likewise, where the immunotherapy is used to treat house dust mite allergy, the allergen administered for immunotherapy may be a house dust mite extract of one or several genera of dust mites such as *Dermatophagoides pteronyssinus* and *Dermatophagoides farinae*.

The allergen may also be an allergoid, i.e. a chemically modified form of a naturally occurring allergen which has been chemically modified (for example by aldehydation). The allergen may be administered in conjunction with an adjuvant.

Immunotherapy may further comprise administration of an additional agent. Said additional agent is preferably administered to a patient undergoing allergen immunotherapy. For example, it may be administered with the allergen in the course of the immunotherapeutic regime, or administered as an additional agent to a patient undergoing or who has undergone allergen immunotherapy. Said additional agent may be formulated with the allergen and administered in combination with the allergen, administered simultaneously with the allergen but in separate form, or administered separately as an adjunct to allergen administration.

'Response' of a patient to treatment indicates that the patient manifests a reduction in the clinical symptoms of allergy. Clinical symptoms may be assessed over the course of treatment, i.e. symptoms before treatment may be compared to symptoms during and after treatment. Alternatively, a reduction in symptoms may be determined by comparison to a baseline level established before treatment. The baseline level may be established on the basis or not of a provocation test. This approach is particularly useful where, for example, immunotherapy is carried out in patients not currently experiencing symptoms, as may be the case for seasonal grass pollen allergy sufferers, who may be treated before the pollen season. Symptoms may be assessed by standard methods, such patient self-assessment or record of the amount of medication required. The degree of a patient's response to treatment may be assessed by measuring the degree of reduction of severity in symptoms, for example as described in the experimental section below.

A 'responder' subject as defined herein is a subject who responds to immunotherapy with an improvement in clinical symptoms higher than patients receiving placebo or no treatment. Preferably, a responder subject will demonstrate an improvement in clinical symptoms which is equal or similar or greater than the average or median improvement seen in a random sample of subjects receiving treatment.

A 'non-responder' subject is a subject who does not manifest any improvement in clinical symptoms following immunotherapy, or who demonstrates an improvement in clinical symptoms which is equal or similar or less as compared to patients receiving placebo or no treatment.

For example, improvement in clinical symptoms for type 1 hypersensitivity or allergy may be detected by:
  a reduction in the frequency or severity of nasal congestion, nasal pruritis, ocular pruritis, tearing, rhinorrhoea, sinusitis, rhinitis, sneezing, wheezing, conjunctivitis, dermal itching, dermatitis, skin irritation, vomiting, stomach cramps, indigestion, diarrhea, hives, shortness of breath, repetitive cough, trouble swallowing, swelling of the tongue and/or lips, weak pulse, dizziness or confusion and asthma, and/or
  reduction in the uptake of known relief medication such as anti-histaminic, corticosteroids, bronchodilatator agents or antileukotriene agents.

Moreover, improvement of clinical symptoms may also be demonstrated on the basis of a combination thereof such as Symptoms Score (e.g. Rhinoconjunctivitis Total Symptom Score (RTSS) or Average Rhinoconjunctivitis Total Symptom Score (ARTSS)), Medication Score (e.g. Rescue Medication Score (RMS) or Average Rescue Medication Score (ARMS)), Combined Scores (e.g. Combined Symptoms Score (CS), Average Combined Symptoms Score (ACS)) (See Clark J. et al., Allergy 2007: 62: 1023-1028; Pfaar et al., Allergy 2014: 69: 854-867).

'Therapy', 'therapeutic', 'treatment' or 'treating' include reducing, alleviating or inhibiting or eliminating the symptoms of allergy, as well as treatment intended to reduce, alleviate, inhibit or eliminate said symptoms. These terms may include preventive treatment which is intended to, or has the effect of, reducing, alleviating, inhibiting or eliminate future symptoms. They may also include treatment of ongoing symptoms.

'Patient' includes any individual who is a candidate for immunotherapy, including individuals not currently undergoing therapy. In most cases, the patient will be an individual who has, or has had at any time in the past, clinical symptoms of allergy and/or sensitization to an allergen and/or an allergen-specific IgE response, or an individual at risk of developing such symptoms. Sensitisation to an allergen may be assessed by detecting IgE directed against allergen(s) from this source in the serum of the patient or by skin testing with a preparation containing the corresponding allergen(s). The allergen may without limitation include any of the allergens disclosed herein, in particular a grass pollen allergen or a house dust mite allergen. The patient preferably has grass pollen allergy or house dust mite allergy, and more preferably allergy to pollen from one or more of *Dactylis, Poa, Lolium, Anthoxanthum, Phleum* and *Dermatophagoides* genera. The patient is preferably a mammal, such as a rodent, a feline, a canine or a primate, and is preferably a human, in particular a child, a woman, a man.

All documents referred to herein are hereby incorporated by reference in their entirety.

Throughout the instant application, the term "comprising" is to be interpreted as encompassing all specifically mentioned features as well optional, additional, unspecified ones. As used herein, the use of the term "comprising" also encompasses the embodiment wherein no features other than the specifically mentioned features are present (i.e. "consisting of") as well as the embodiment wherein features other than the specifically mentioned feature are present provided that the essential characteristics of the composition are not materially affected by their presence (i.e. "consisting essentially of").

The present invention will be further illustrated by the following figures and examples. It should be understood however that these examples are given only by way of illustration of the invention and do not constitute in any way a limitation thereof.

BRIEF DESCRIPTION OF THE SEQUENCES

SEQ ID NO: 1 shows the sequence of reference Fetuin-A polypeptide.
SEQ ID NO: 2 shows the sequence of a first fragment of Fetuin-A.
SEQ ID NO: 3 shows the sequence of a second fragment of Fetuin-A.
SEQ ID NO: 4 shows the sequence of a third fragment of Fetuin-A.

SEQ ID NO: 5 shows the sequence of a fourth fragment of Fetuin-A.
SEQ ID NO: 6 shows the sequence of a fifth fragment of Fetuin-A.
SEQ ID NO: 7 shows the sequence of a sixth fragment of Fetuin-A.
SEQ ID NO: 8 shows the sequence of a seventh fragment of Fetuin-A.
SEQ ID NO: 9 shows the sequence of an eighth fragment of Fetuin-A.
SEQ ID NO: 10 shows the sequence of a ninth fragment of Fetuin-A.
SEQ ID NO: 11 shows the sequence of a tenth fragment of Fetuin-A.
SEQ ID NO: 12 shows the sequence of an eleventh fragment of Fetuin-A.
SEQ ID NO: 13 shows the sequence of a twelfth fragment of Fetuin-A.
SEQ ID NO: 14 shows the sequence of a thirteenth fragment of Fetuin-A.
SEQ ID NO: 15 shows the sequence of a fourteenth fragment of Fetuin-A.
SEQ ID NO: 16 shows the sequence of a fifteenth fragment of Fetuin-A.
SEQ ID NO: 17 shows the sequence of a sixteenth fragment of Fetuin-A.
SEQ ID NO: 18 shows the sequence of a seventeenth fragment of Fetuin-A.
SEQ ID NO: 19 shows the sequence of an eighteenth fragment of Fetuin-A.
SEQ ID NO: 20 shows the sequence of a nineteenth fragment of Fetuin-A.
SEQ ID NO: 21 shows the sequence of a twentieth fragment of Fetuin-A.
SEQ ID NO: 22 shows the sequence of a twenty-first fragment of Fetuin-A.
SEQ ID NO: 23 shows the sequence of a twenty-second fragment of Fetuin-A.
SEQ ID NO: 24 shows the sequence of a twenty-third fragment of Fetuin-A.
SEQ ID NO: 25 shows the sequence of a twenty-fourth fragment of Fetuin-A.
SEQ ID NO: 26 shows the sequence of a twenty-fifth fragment of Fetuin-A.
SEQ ID NO: 27 shows the sequence of a twenty-sixth fragment of Fetuin-A.
SEQ ID NO: 28 shows the sequence of a first fragment of Fetuin-B.
SEQ ID NO: 29 shows the sequence of a second fragment of Fetuin-B.
SEQ ID NO: 30 shows the sequence of a third fragment of Fetuin-B.

BRIEF DESCRIPTION OF THE FIGURES

FIG. 4: Post-translational variants OG1, OG2 and OG3 of Fetuin A analyzed by mass spectrometry diamond stands for sialic acid or N-acetylneuraminic acid (Neu5Ac or NeuAc), circle for galactose (Gal), and square for N-acetylgalactosamine (GalNAc). OG3 consists of SEQ ID NO:2 comprising an O-linked oligosaccharide chain bearing two terminal sialic acid residues at position 256 and an O-linked oligosaccharide chain bearing two terminal sialic acid residues at position 270. OG2 consists of SEQ ID NO:2 comprising an O-linked oligosaccharide chain bearing one terminal sialic acid residue at position 256 and an O-linked oligosaccharide chain bearing two terminal sialic acid residues at position 270

FIG. 9: ROC curves of OG3 abundance levels of 42 treated patients (AUC: area under the ROC curve), threshold to generate groups: (A) Percentage of ARTSS improvement=50%, (B) Percentage of ARTSS improvement=10%. OG3 consists of SEQ ID NO:2 comprising an O-linked oligosaccharide chain bearing two terminal sialic acid residues at position 256 and an O-linked oligosaccharide chain bearing two terminal sialic acid residues at position 270). In these ROC curves, controls are defined as responder patients (i.e. patients with a percentage of improvement in ARTSS greater than or equal to the percentage of ARTSS improvement thresholds defined above).

FIG. 11: Sialylated Fetuin-A but not desialylated Fetuin-A synergizes with LPS to engage the TLR4 pathway.

Figure 1:
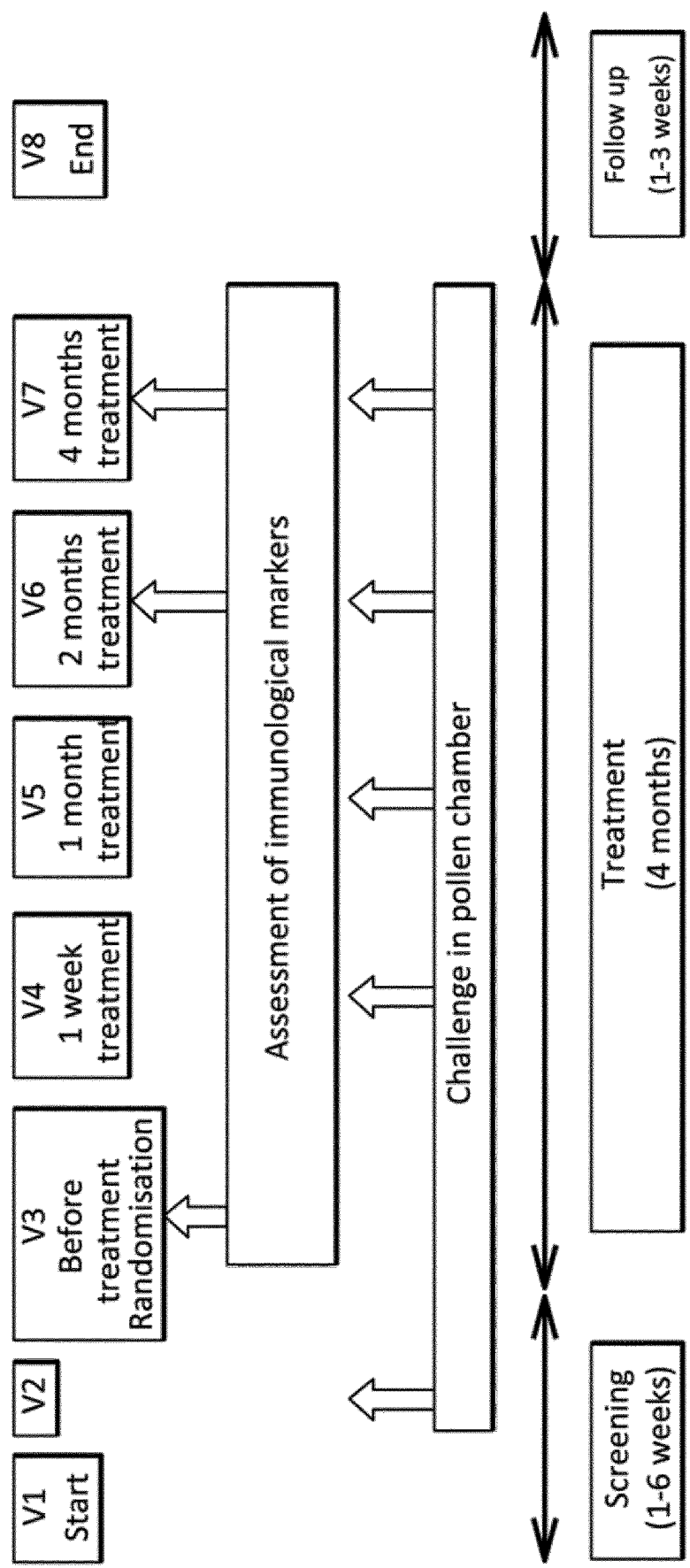
FIG. 1: Study design. Following screening and randomization, patients were treated once daily with either a placebo or a 5-grass pollen tablet for 4 months. Grass pollen challenges were performed before treatment and at day 7, and at months 1, 2 and 4, concomitantly with evaluation of ARTSS. The search for predictive biomarkers was performed on 82 serum samples collected from patients before treatment initiation.

a) Optical density values (OD at 655 nm) after 18 hours of stimulation of hTLR4 HEK-293 reporting cells incubated with increasing doses of either LPS, Sialylated Fetuin-A or a combination of both. * and #indicate a statistically significant difference versus Sialylated Fetuin-A-stimulated or LPS-stimulated hTLR4 HEK-293 cells respectively, using a two-way ANOVA test with Tukey's correction. b) The expression of CD80, CD83 and CD86 co-stimulatory markers was assessed at the surface of MoDCs by flow cytometry. c) Cytokine production by stimulated DCs was measured using a Luminex assay. Data are shown as means±SEM (n=4) in FIGS. 4b and 4c. d) hTLR4 HEK-293 reporting cells were stimulated with either LPS (100 ng/mL), Sialylated Fetuin-A (10 µg/mL), Desialylated Fetuin-A (10 µg/mL) or combinations of those molecules. OD values were measured at 655 nm after 18 hours of incubation. e) Cell surface expression of co-stimulatory molecules was assessed by flow cytometry on stimulated MoDCs and f) cytokine production was measured using a Luminex assay. Data are shown as means±SEM (n=6) in FIGS. 4e and 4f. A p-value≤0.05 is considered significant (Friedman test).

FIG. 12: Sialylated Fetuin-A, but not Desialylated Fetuin-A, enhances specific DC2 pro-inflammatory characteristics.

a) DC2s cultured for 24 hours in serum-free medium in presence of Sialylated Fetuin-A or Desialylated Fetuin-A were tested for expression of co-stimulatory molecules (CD80, CD83 and CD86) by flow cytometry. b) Cytokine production was measured using a Luminex assay. c) Expression of DC1, DC2 or DCreg-related genes was measured by real-time PCR. Data are shown as means±SEM (n=4) in FIG. 5a to c. d) Cytokine production by DC2s cultured in presence of Sialylated Fetuin-A or Desialylated Fetuin-A (both at 10 µg/mL) and a 5 grass pollen extract (20 µg/mL) was measured using a Luminex assay. Results are presented for n=6 (out of 12 donors tested) as means±SEM. e) Quantification of IL-6 and IL-10 produced by DCs in presence of Sialylated Fetuin-A or Desialylated Fetuin-A (both at 10 µg/mL) and a D. far. (1 µg/mL) extract was performed using a Luminex assay (means±SEM on n=6 donors).

FIG. 13: ROC curves of OG3 abundance levels of 42 treated patients (AUC: area under the ROC curve) in which the controls are defined as non-responder patients (i.e. patients with a percentage of improvement in ARTSS lower than a threshold). Threshold used to generate groups: (A) Percentage of ARTSS improvement=50%, (B) Percentage of ARTSS improvement=43.9%, (C) Percentage of ARTSS improvement=10%. OG3 consists of SEQ ID NO:2 comprising an O-linked oligosaccharide chain bearing two terminal sialic acid residues at position 256 and an O-linked oligosaccharide chain bearing two terminal sialic acid residues at position 270).

EXAMPLES

Example 1

Materials and Methods

Clinical Samples from VO56.07A Pollen Chamber Study

Eighty-nine allergic patients were randomized 1:1 to receive either a grass pollen or placebo tablet through the sublingual route. Challenges were performed before treatment and after 1 week and 1, 2, and 4 months of treatment. Because patients were challenged before treatment, individual clinical responses were evaluated by calculating percentages of improvement in Average Rhinoconjunctivitis Total Symptom Scores (ARTSSs) between baseline and after 4 months of treatment. The median percentage ARTSS improvement in the active group (corresponding to at least a 43.9% decrease of ARTSS after treatment) was considered a threshold to identify clinical responders. Subjects with a percentage of ARTSS improvement greater than or equal to this threshold were considered responders, and those with improvement lower than the threshold were considered non-responders. Whole blood was collected in 82 patients before and after treatment for immunological measurements, cellular assays or comparative proteomics experiments: 4 patient subgroups, including active responders (ARs; n=21), active non-responders (ANRs; n=21), placebo responders (PRs; n=7), and placebo non-responders (PNRs; n=33).

Affinity Depletion of High Abundance Proteins for Proteomics Analyses

Serum samples (340 µL each) were processed using a human Multiple Affinity Removal System (MARS) Human 6 (Hu-6HC column, 10×100 mm, Agilent Technologies, Les-Ulis, France), which selectively and specifically removed albumin, IgG, antitrypsin, IgA, transferrin and haptoglobin. An Ultimate 3000 HPLC (Thermo scientific, Villebon-sur-Yvette-Courtaboeuf, France) consisting of a binary pump, a thermostatted autosampler with extended injection volume option, a thermostatted column compartment, a diode array detector, and a thermostatted analytical scale fraction collector was used for the affinity chromatography. Flow-through proteins were collected and concentrated according to the manufacturer's instructions (Hu-6HC column, Agilent Technologies). Samples were stored at −80° C. until analysis and run-to-run reproducibility of depletion was confirmed with the chromatographic data and SDS-PAGE analysis under reducing conditions (4-12% NuPAGE gel, Life Technologies, Saint-Aubin, France).

Two-Dimensional DiGE Experimental Design

Serum samples were precipitated with 2D clean-up kit according to GE Healthcare's protocol (Velizy-Villacoublay, France), solubilized in a buffer containing 7 M urea, 2 M thiourea, 4% CHAPS and 30 mM Tris pH 8.8 (all obtained from Sigma-Aldrich, Saint-Quentin-Fallavier, France) and stored at −80° C. Protein concentrations were determined by means of the Bradford assay (Bio-Rad, Marnes-la-Coquette, France) and depleted serum proteins (50 µg) were minimally labeled with 400 pmol of Cy2 (internal standard), Cy3, or Cy5 DiGE fluors (GE Healthcare) as described in the instruction manual. Samples consisted of depleted serum from ARs (n=21), ANRs (n=21), PRs (n=7) and PNRs (n=33). A dye-swapping scheme was used to avoid any specific dye-labeling artifacts. The Cy2 internal standard was obtained by pooling equal amounts of proteins (25 μg) from all 82 patients sera included in analysis. Two SDS-PAGE tests were performed, with each gel containing two different samples (Cy3- and Cy5-labeled) and an internal standard sample (Cy2-labeled). Protein samples labeled with Cy2, Cy3, and Cy5 dyes were then mixed and diluted with rehydration buffer, containing 7 M urea, 2 M thiourea, 4% CHAPS, 100 mM DTT, 0.5% IPG pH 4-7 buffer, to a final volume of 450 μl. 150 μg (combination of the three labeled protein samples) of protein was applied to 24-cm-long immobilized pH 4-7 gradient strips (GE Healthcare) via the passive rehydration technique for 15 h. First-dimension isoelectric focusing (IEF) was performed using an IPGPhor 3 electrophoresis unit (GE Healthcare) cooled to 18° C. for a total of 74 kVh. After IEF, strips were equilibrated in urea-containing buffer for full protein reduction, alkylation and placed on top of pre-cast SDS-containing 12.5% polyacrylamide gels (GE Healthcare). SDS-PAGE was carried out at 0.5 W per gel for 1 h followed by 1 W per gel for 16 h (Ettan DALT Twelve Electrophoresis System, GE Healthcare). DiGE gels were scanned using an Ettan DiGE Imager (GE Healthcare) according to the manufacturer's instructions. Based on quality control gel, gel number 79 was excluded from analysis (i.e. ANR sample). Differentially expressed spots were determined by image analysis with SameSpots program (Nonlinear Dynamics, Newcastle upon Tyne, UK) and selected for automatic spot picking (EXquest™ Spot Cutter, Bio-Rad). Preparative gels post-stained with Sypro Ruby (Life Technologies) were used for spot picking and protein identification was performed by tandem mass spectrometry (MS/MS).

Identification of Protein Spots by Tandem Mass Spectrometry

Gel plugs were digested with trypsin and peptides were separated by reversed-phase chromatography using an Ultimate 3000 RS-nanoLC system (Thermo scientific). Peptides were injected and trapped on an Acclaim® PepMap100 (100 μm×2 cm; $C_{18}$, 5 μm particles and pore size at 100 Å, Thermo scientific) and separation was then performed using a $C_{18}$ column (Acclaim® PepMap RSLC 75 μm ID, 15 cm, 2 μm particles, and pore size at 100 Å, Thermo Scientific). The nanoLC system was coupled to a high-resolution maXis 4G ESI-Qq-TOF mass spectrometer (Bruker Daltonics, Wissembourg, France). NanoLC-MS/MS data were analyzed using an in-house Mascot server (Matrix Science Ltd, London, UK) or PEAKS program (Bioinformatics Solutions Inc., Waterloo, Canada) to search public databases such as the Uniprot/Swiss-Prot database and the nonredundant National Center for Biotechnology Information (nrNCBI) database, assuming tryptic digestion. Precursor mass and fragment mass were searched with initial mass tolerance of 8 ppm and 0.05 Da, respectively. The search included fixed modification of carbamidomethyl (CAM) cysteine. Minimal peptide length was set to 6 amino acids and a maximum of one miscleavage was allowed. Peptide identifications were accepted if they could be established at a greater than 95% probability as specified by Mascot or PEAKS software.

Quantitation by Label-Free Mass Spectrometry

50 μg of serum proteins were mixed with a urea-containing buffer, reduced with 20 mM DTT, alkylated with 50 mM iodoacetamide and digested with trypsin (37° C., overnight, enzyme/substrate ratio of 1/25). After digestion, peptides were acidified with 2.5% FA and analyzed by LC-MS or LC-MS/MS using the Ultimate 3000 RSLC system coupled to a maXis 4G ESI-Qq-TOF mass spectrometer. 5 μg of tryptic peptides were injected on an Acquity $C_{18}$ BEH130 column (10 mm ID, 10 cm, 1.7 μm particles, Waters) equilibrated at 40° C. with 95% solvent A (0.15% FA); 5% solvent B (100% ACN 0.15% formic acid) at a flow rate of 0.4 mL/min. Separation was performed at a flow rate of 0.4 ml/min with a linear gradient from 5 to 40% solvent B over 30 min. Ion intensities recorded in LC-MS data were analyzed using Progenesis LC-MS v4.1 software (Nonlinear Dynamics, Newcastle upon Tyne, UK) to provide reliable measurements of peptide abundance across samples. Lock mass calibration was performed and peptide detection was performed with peptide intensity>1000, peptide abundance>2000 and 2+≤peptide charge≤12+. Data were then normalized by the "normalize to all features" method and comparison between the four groups (obtained from ARs, ANRs, PRs and PNRs) was performed to choose which peptides were statistically differentially represented. LC-MS/MS data were analyzed using an in-house Mascot server against the Swiss-Prot database, taxonomy Homo sapiens, assuming tryptic or semi-tryptic digestion as described above, and were subsequently imported into software.

Enzymatic Desialylation and Characterization of Human Fetuin-A 31.15 μg of native purified Fetuin-A were mixed with 10 μL of 5× Reaction Buffer (EDEGLY kit, Sigma). 1 μL of α-(2→3,6,8,9)-Neuraminidase was added (EDEGLY kit, Sigma), to reach a final enzymatic activity of 0.109 U/mL, and the mixture was incubated overnight at 37° C. Desialylation efficiency was assessed by SDS-PAGE and MS characterization.

Mass Spectrometry Analyses of Purified Fetuin A

Measurements of average mass (Mav) of intact proteins were performed on a maXis ESI-Qq-TOF mass spectrometer coupled to an Ultimate 3000 RSLC system (Thermo Scientific). Proteins were denatured and reduced in a buffer containing 8M urea, 75 mM Tris pH 8.5, 20 mM DTT for 20 min and acidified by 2.5% formic acid (FA). Protein samples were then desalted and concentrated for 4 min onto a Acquity $C_4$ BEH300 column (10 mm ID, 10 cm, 1.7 μm particles, Waters, Saint-Quentin-en-Yvelines, France) equilibrated at 70° C. with 95% solvent A (0.15% FA); 5% solvent B (100% ACN 0.15% formic acid) at a flow rate of 0.4 mL/min. Proteins were eluted directly into the mass spectrometer at a flow rate of 0.4 mL/min with a linear gradient from 5 to 60% solvent B over 30 min. Mass spectra were deconvoluted using MaxEnt, and the precise Mav of proteins was determined with Data Analysis (Bruker Daltonic).

The presence of post-translational modifications (PTMs) on purified proteins was determined by nanoLC-MS/MS as described above. Purified Fetuin A or desialylated Fetuin A proteins were solubilized in a buffer containing 8 M urea, 75 mM Tris pH 8.5 and 5 mM TCEP. Proteins were then alkylated with iodoacetamide (10 mM) for 20 min and subjected to a trypsin digestion in-solution (protein/protease mass ratio 50/1) for 3 h at 37° C. in presence of 0.018% of ProteaseMax surfactant (Promega, Charbonnieres, France). 2.5% FA was added to the mixture to quench enzymatic activity and peptides were stored at −80° C. until the day of analysis. Peptide samples were then spun at 18000 g and the peptide mixture was separated using a $C_{18}$ column (Acclaim® PepMap RSLC 75 μm ID, 25 cm, 2 μm particles, and pore size at 100 Å, Thermo Scientific). N- and O-glycopeptides were manually identified by the presence of glycan-specific oxonium ion fragments.

Immunomodulatory Properties of Sialylated Fetuin-A and Desialylated Fetuin-A

Monocytes isolated from PBMCs of healthy volunteers with CD14 microbeads (Miltenyi Biotec, Bergisch Gladbach, Germany) were cultured in presence of GM-CSF and IL-4 (Miltenyi Biotec) for 6 days. DC differentiation was confirmed by flow cytometry based on the loss of CD14 expression and the upregulation of CD1a and CD11c surface expression. Immature monocyte-derived DCs (MoDCs) or MoDCs polarized towards a DC2 pattern were cultured in serum free medium (CellGro DC medium, Cellgenix, Freiburg, Germany) for 24 hours, in presence of either medium alone, or medium supplemented with either ultrapure LPS-EB from *Escherichia coli* (100 ng/mL, Invivogen, Toulouse, France), native purified sialylated Fetuin-A (10 µg/mL), desialylated Fetuin-A (10 µg/mL), a 5-grass pollen (from *Lolium perenne, Poa pratensis, Phleum pratense, Dactylis glomerata* and *Anthoxanthum odoratum*) or *Dermatophagoïdes farinae* allergen extracts (20 or 1 µg/mL, respectively, Stallergenes SA, Antony, France), or combinations of these reagents. In some experiments, the TLR4 pathway was blocked by adding LPS from *Rhodobacter sphaeroides* (LPS-RS, 10 µg/mL, Invivogen) to MoDCs for 30 minutes. Supernatants were harvested to measure cytokine (IL-1β, IL-6, IL-8, IL-10, IL-12p70 and TNF-α) production using a Luminex assay (Milliplex, Millipore). Surface expression of maturation markers (CD80, CD83 and CD86,) was assessed on DCs by flow cytometry (BD Biosciences, San Jose, US). Total RNA (RNeasy Mini Kit, Qiagen, Venlo, Netherlands) was isolated to evaluate the expression of C1QA, MX1, and PADI2 genes by real-time PCR using β-actin as an endogenous reference gene (the following primers, all from Thermo scientific, were used: Hs00381122_m1, Hs00895608_m1 and Hs00247108_m1, respectively).

Statistical Analysis

Data are expressed as means±SEMs. Statistical differences between groups were assessed by using 2-tailed nonparametric Mann-Whitney test or by using 2-tailed parametric t-test and the Friedman test for multiple comparisons. Correlation analyses were performed by using the nonparametric Spearman test, or the parametric Pearson test. p-values of less than 0.05 were considered significant. Statistical and graphic analyses were performed with GraphPrism 5 software (GraphPad Software, Inc, La Jolla, Calif.). Significant differences in protein expression changes in DiGE analysis, and in peptide abundance in label-free MS experiments were assessed by using an anova p-value threshold of 0.01. A fold-change filter (≥1.5) was also used. Statistics on proteomic data were performed with two programs from Nonlinear Dynamics (Newcastle upon Tyne, United Kingdom) called Samespots or Progenesis LC-MS.

Example 2

Results

Sialylation of Serum Fetuin A Discriminates Clinical Responders

Figure 2:
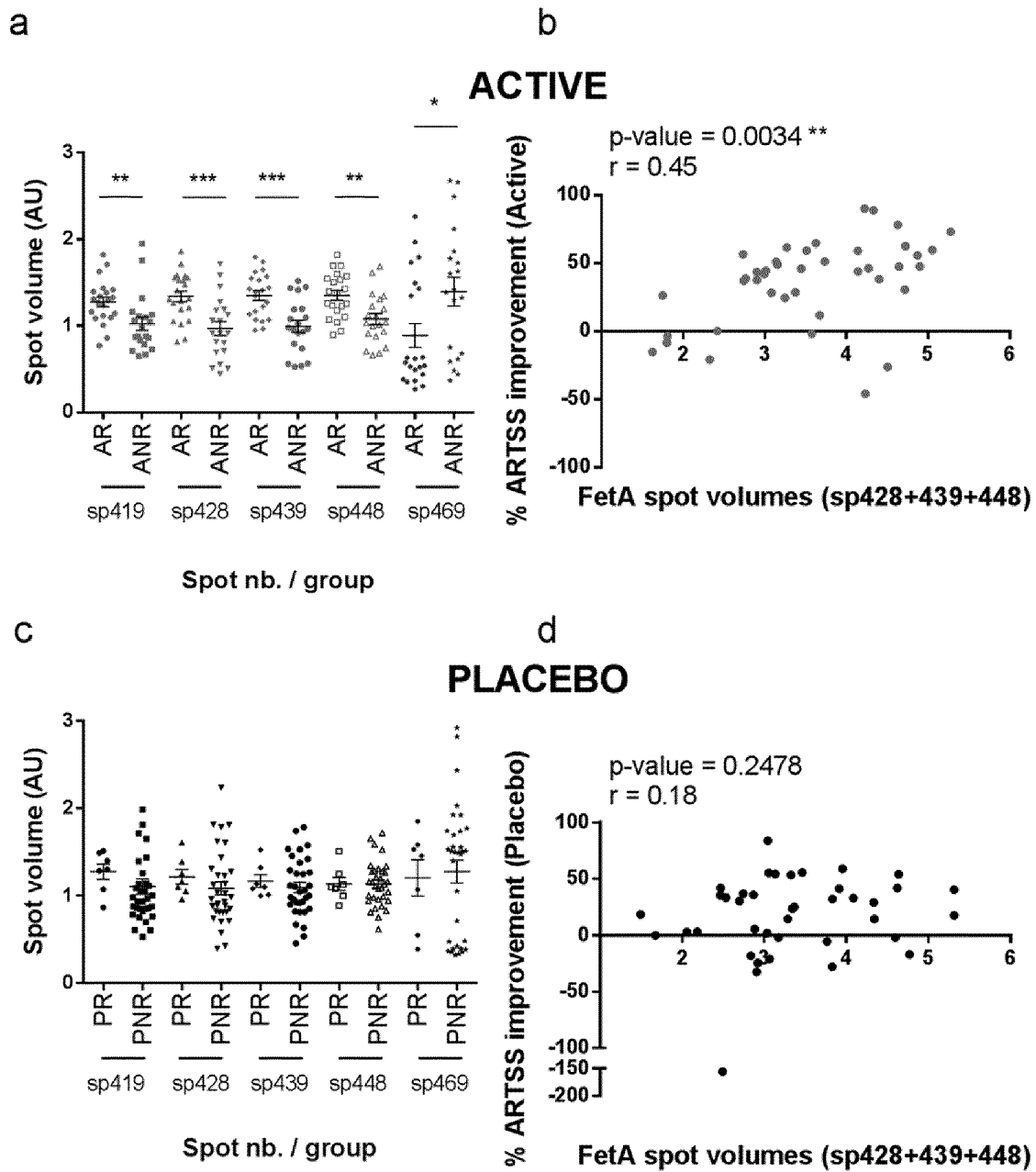
FIG. 2: Abundances of Fetuin A protein spots measured by 2D-DiGE as mean±SEM in active (A) and placebo (C) groups, and Spearman correlations between Fetuin A abundances and percentages of ARTSS improvement in patients from active (B) and placebo (D) groups after 4 months of AIT. Fetuin A spots are numbered based on their isoelectric point. 4 patient subgroups are defined based on the median percentage of improvement in ARTSS in the active group: active responders (ARs, n=21), active non responders (ANRs, n=20), placebo responders (PRs, n=7), and placebo non responders (PNRs, n=33)

The clinical study described in Example 1 was used to compare serum proteome profiles and predict clinical responders from non-responders to treatment with AIT. Serum samples, from 4 patient subgroups, including active responders (ARs; n=21), active non-responders (ANRs; n=20), placebo responders (PRs; n=7), and placebo non-responders (PNRs; n=33) were retrospectively compared by using 2D-DiGE. After immune-affinity depletion of the top 6 high abundant proteins to enhance the detection of lower abundance proteins, protein spots whose volume was significantly different between subgroups were cut out from 2D-gels, trypsin digested and analyzed by mass spectrometry (MS). Differences in levels of expression of Fetuin A protein spots (also termed Alpha-2-HS-glycoprotein, AHSG) were observed between AR and ANR patients (FIG. 2). The abundance of four proteoforms of A chain (sp419, 428, 439 and 448) was increased in AR individuals (p<0.01 or 0.001, FIG. 2A) whereas the one of sp469 was decreased (p<0.05). When plotted against percentages of symptom score improvement for each individual patient, the abundance of the more acidic spots, i.e. sum of sp419, 428 and 439, was significantly correlated with clinical benefit in patients from the active group (with Spearman correlation of r=0.5, p=0.0009, FIG. 2B), whereas no difference in levels of expression and no such correlation were observed in placebo-treated patients (FIG. 2C-D). Collectively, those observations indicate that Fetuin A-spot train could shift toward acidic pH values, suggesting post-translational modification (PTM) changes in AR patients.

Figure 3:
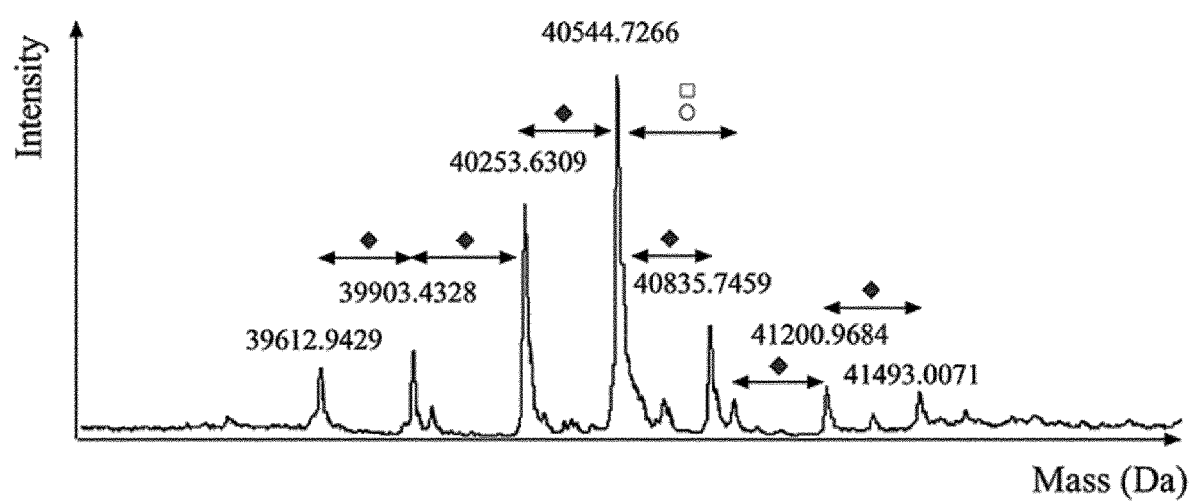
FIG. 3: Measurement of intact mass of the A chain of purified Fetuin A from healthy human serum by mass spectrometry.
Figure 6:
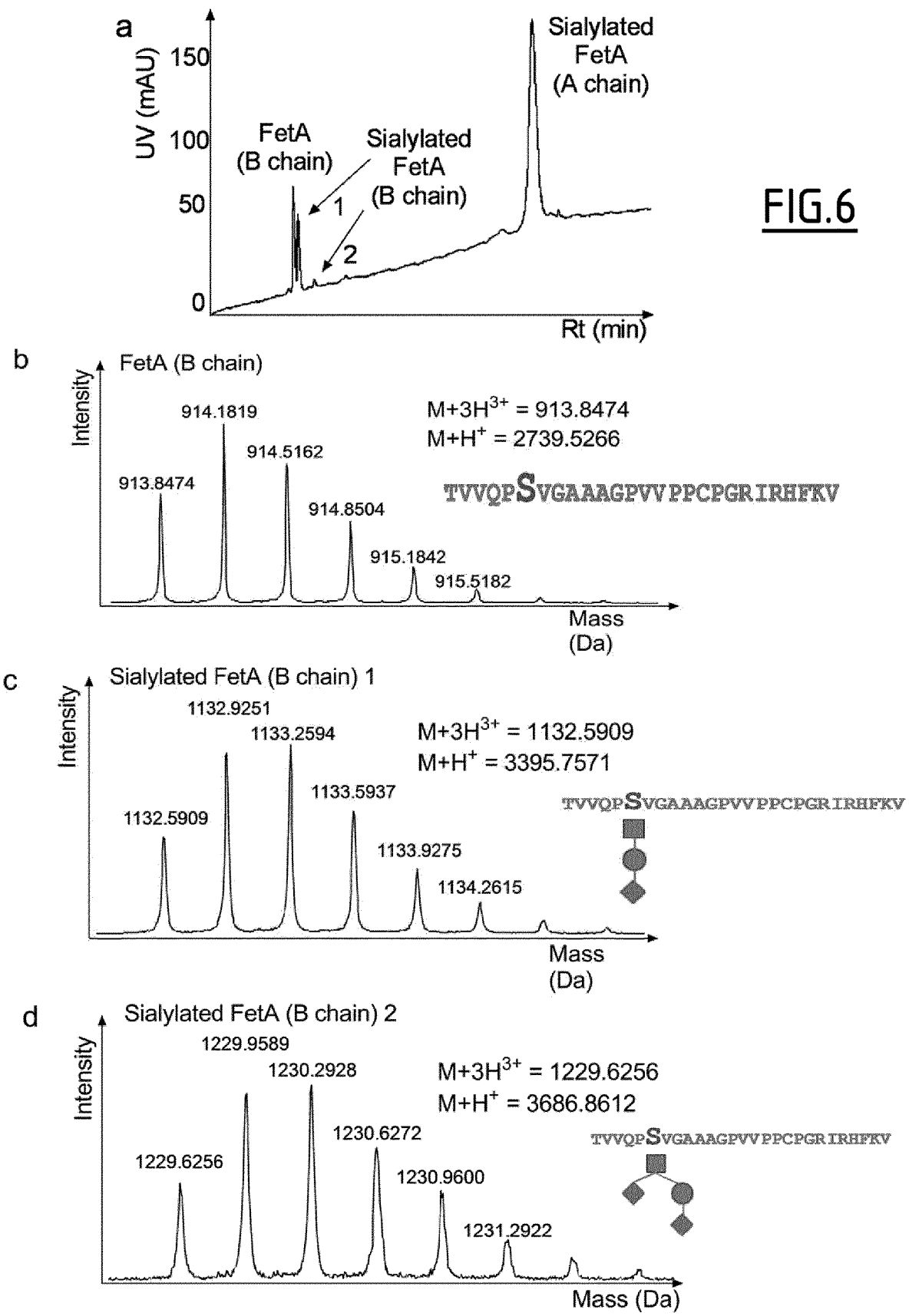
FIG. 6: Measurement of intact mass of purified sialylated Fetuin A from healthy human serum by mass spectrometry.
a) LC-UV analysis of the reduced forms of natural FetA (in a 20 mM DTT containing buffer). b-d) Mass spectrometry analysis of B chain. Non-glycosylated (b) and sialylated forms (O-linked glycans) can be observed on the mass spectrum (c, d). Square=N-acetylglucosamine; circle=hexose; diamond=N-acetylneuraminic acid (sialic acid).
Figure 7:
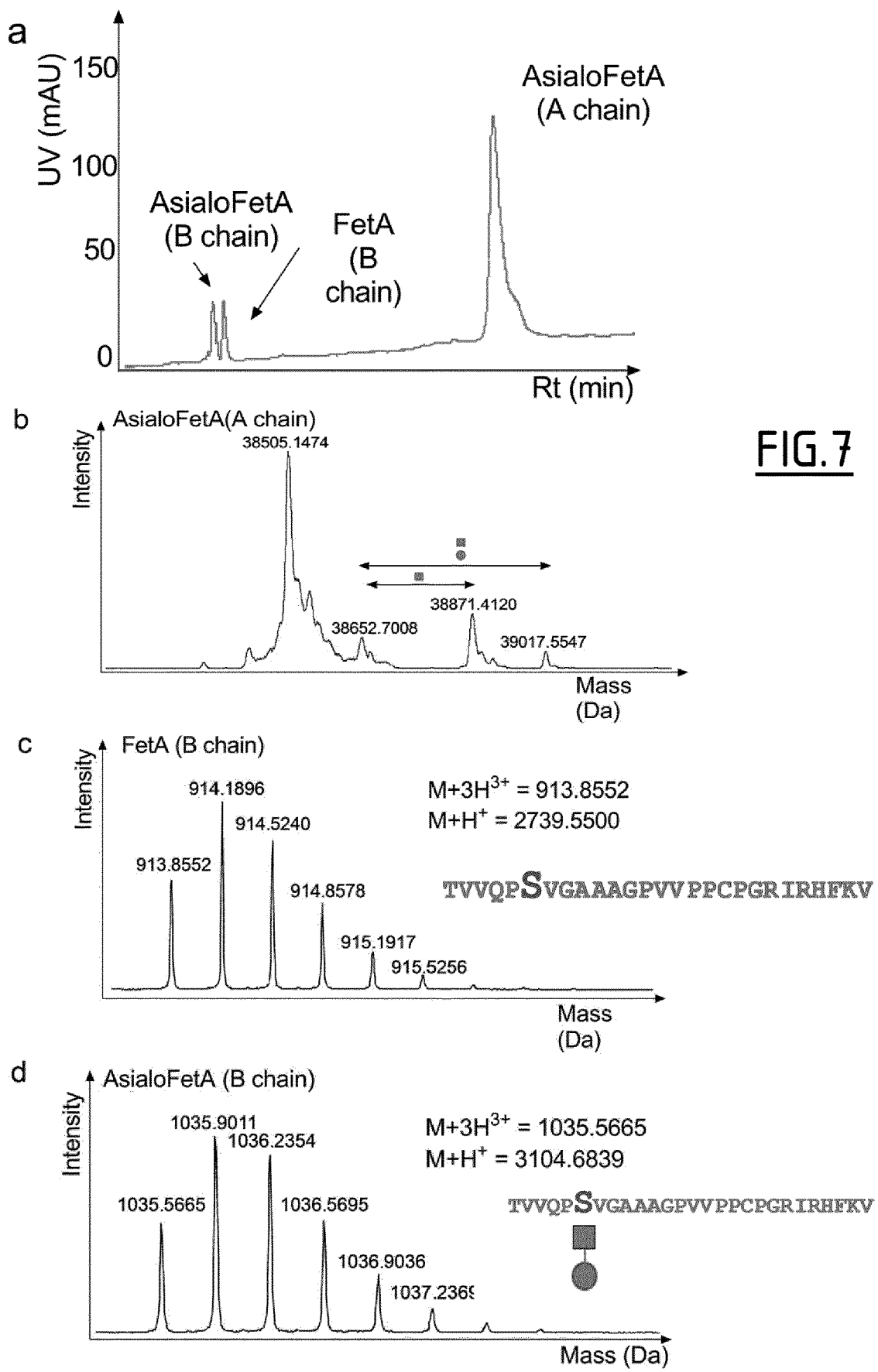
FIG. 7: Measurement of intact mass of purified desialylated Fetuin A from healthy human serum by mass spectrometry.
a) LC-UV analysis of the reduced forms of natural FetA (20 mM DTT).
b-d) Mass spectrometry analysis of A chain (b) and B chain (c-d). Square=N-acetylglucosamine; circle=hexose; diamond=N-acetylneuraminic acid (sialic acid). The term AsialoFetA means Fetuin A desialylated.

The inventors subsequently purified Fetuin A from healthy human serum by affinity chromatography to gain further insight into the type of PTMs associated. The A chain resolved on SDS-PAGE as a single band at ~40 kDa and measurements of intact mass by using MS revealed the contribution of a large number of sialic acid (Neu5Ac) branched on glycan moieties (FIG. 3 and FIG. 6A). Strikingly, Neu5Ac is anionic and therefore likely contributes to Fetuin A's charge and the migration toward acidic pH during 2D-DiGE, as observed in AR donors. The MS analysis also revealed that a portion of B chain is sialylated with one or two Neu5Ac (FIG. 6B-D). Lastly, the treatment of purified Fetuin A with sialidase, attested by MS analysis of asialofetuin A (FIG. 7), markedly changed the 2D-gel profile and allowed the complete disappearance of the spot charge-train.

Taken together, the shift of Fetuin A-spot train toward acidic pH is dependent on sialylation levels, suggesting that the more the patient is responder to AIT, the greater the sialylation of Fetuin A before AIT is.

Sialylation Levels of Fetuin A Depend of O-Linked Oligosaccharide Chains

As a glycoprotein, Fetuin A carries N-linked and O-linked oligosaccharide chains that terminate with sialic acid residues (Swiss-Prot AC P02765) and the inventors observed that the positive AIT response is associated with the increase of sialylated glycoforms before treatment. The inventors thus comprehensively examined for its glycan structures by using MS in order to provide a reliable quantitative comparability of those glycoforms in clinical samples. Glycopeptides, derived from purified Fetuin A by trypsin digestion, were assigned based on a combination of the MS/MS data and the accurate precursor ion mass measurement. Particularly unique to glycopeptides containing sialylated glycans are B-type ions corresponding to neutral mass 291 Da (Neu5Ac) and neutral mass 273 Da (Neu5Ac—$H_2O$). Mass peaks also include those observed as 203 Da, 365 Da, 656 Da, and 947 Da which correspond to the neutral masses of HexNAc, (Hex+HexNAc), (Hex+HexNAc+Neu5Ac) and (Hex+HexNAc+Neu5Ac2). In this work, two sites of N-glycan attachment were evidenced for residues $N_{156}$ and $N_{176}$ and the most abundant N-glycan found was disialylated (Hex5HexNAc4Neu5Ac2, Table 2). In addition to N-glycans, a number of O-glycopeptides were present, mostly attached with sialylated glycans. The O-glycopeptide from A chain contained two mucin-type glycans for residues $T_{256}$ and $T_{270}$ and all of which were sialylated, with one or two Neu5Ac (termed OG1, OG2, and OG3 depending on the number of Neu5Ac, FIG. 4 and Table 2). The B chain was observed in both non-, mono- and disialylated form (residue $S_{346}$, FIG. 6B-D).

Figure 5:
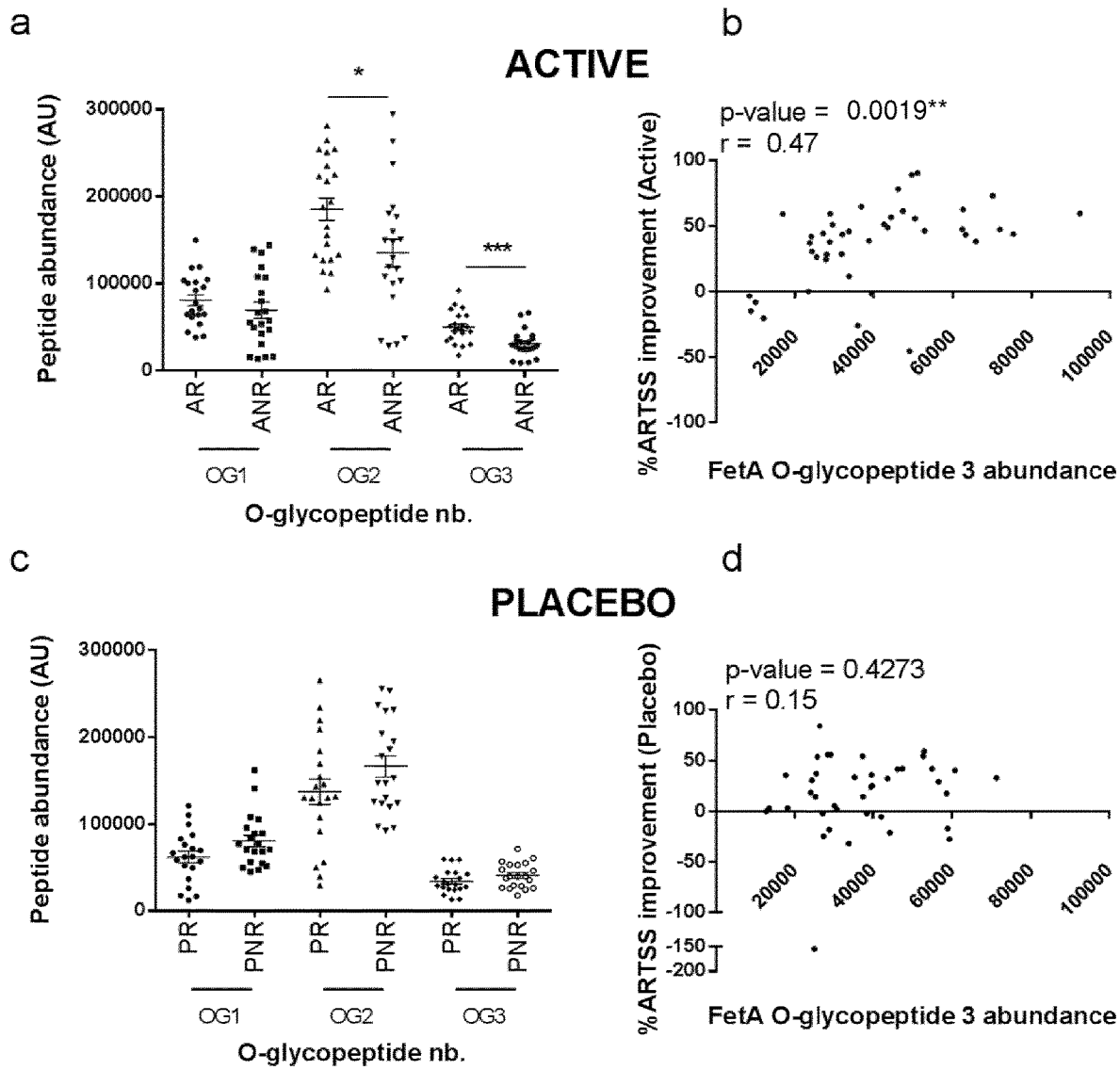
FIG. 5: O-glycopeptide abundances are shown as means±SEM in active (a) and placebo (c) groups. Difference between groups were tested using a Mann-Whitney test (with * and *** indicating p-values≤0.05 and ≤0.001, respectively). Pearson correlation of O-glycopeptide 3 abundance with percentages of ARTSS improvement in patients from active (b) and placebo (d) groups after 4 months of AIT. 4 patient subgroups are defined based on the median percentage of improvement in ARTSS in the active group: active responders (ARs, n=21), active non responders (ANRs, n=21), placebo responders (PRs, n=7), and placebo non responders (PNRs, n=33).
Figure 8:
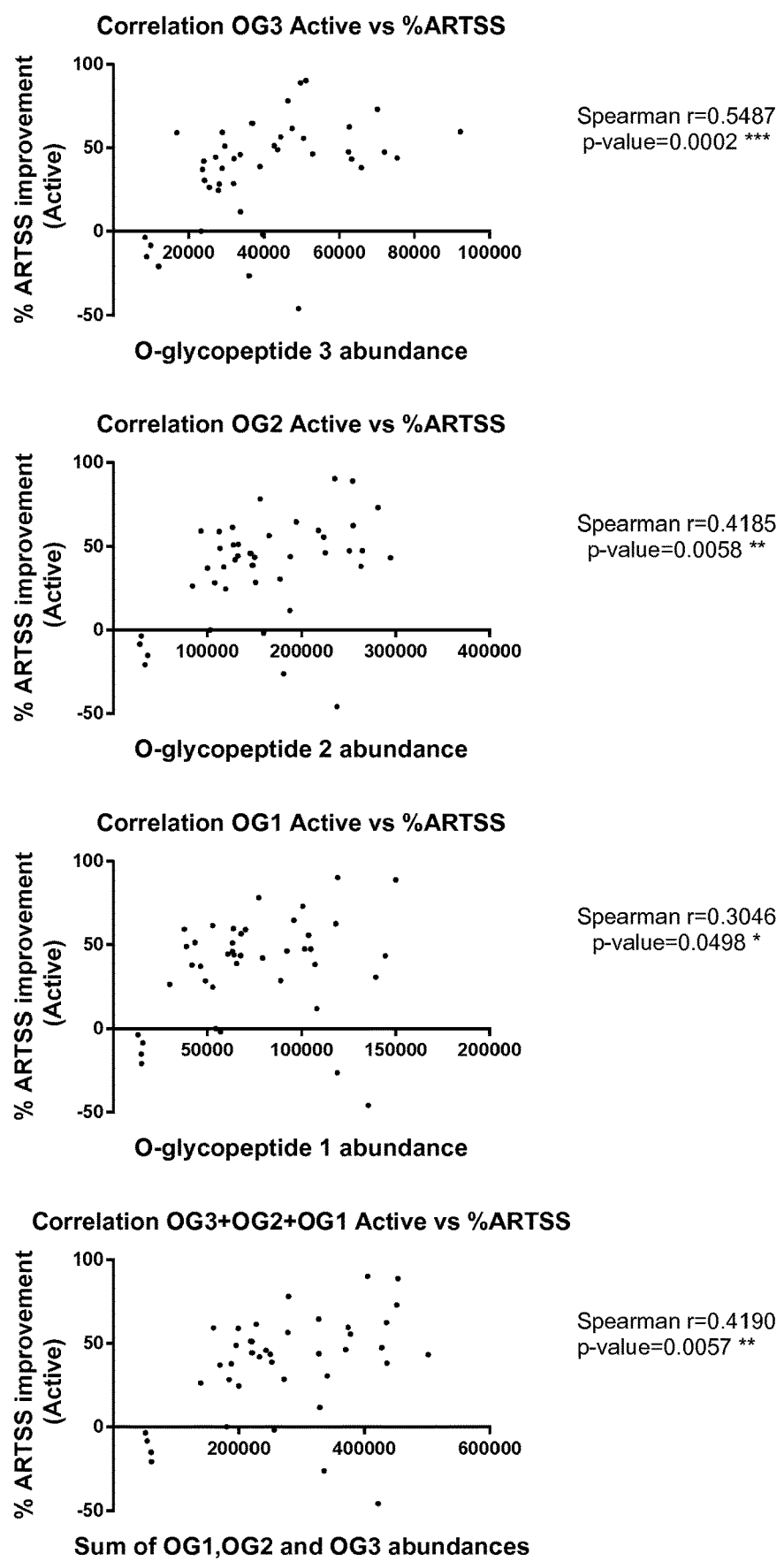
FIG. 8: Spearman correlations between O-glycopeptides abundances and percentages of ARTSS improvement in patients from the active group after 4 months of AIT. OG=O-glycopeptide. Total peptide abundance for a sample of 82 patients (42 treated with active tablets and 40 with placebo)=6379678890; Mean of total peptide abundance per patient=77800962.

Furthermore, considering the site-specific glycosylation of Fetuin A, it is now possible to conduct analysis of clinical samples to understand the diagnostic potential of sialylated Fetuin A. A label-free MS analysis was developed for the direct comparison of MS signals corresponding to Fetuin A-peptides and -glycopeptides (Table 2). With this method in place, the inventors conducted analysis of clinical samples and observed that O-glycopeptides containing core 1 type with two Neu5Acs were the most significantly increased in AR individuals (OG2, $p<0.01$ and OG3, $p<0.001$, FIG. 5A and disialylated B chain $p<0.01$, Table 2). Strikingly, as previously observed for the abundance of the more acidic spots of Fetuin A, the tetrasialylated glycopeptide OG3 significantly correlated with improvement of clinical symptoms in patients from the active group (with Spearman correlation of $r=0.5$, $p=0.0002$, FIG. 5B and FIG. 8), whereas no such correlation were observed in placebo-treated patients (FIG. 5C-D).

In summary, sialylation levels of Fetuin A disiminate clinical responders from non-responders to treatment with grass pollen allergy vaccine and are dependent, at least in part, of the number of Neu5Acs attached to O-linked oligosaccharide chains. The sialylation of Fetuin A may thus play a significant role in its functional heterogeneity.

The inventors showed that the peptide variants herein named OG1, OG2 and OG3 were present at a significantly higher level in the serum of patients that responded well to sublingual immunotherapy. More importantly, although all three peptides showed a significant level of correlation, peptide variant OG3 presented a better statistical correlation with the response to treatment. Similarly, OG3 presented a more significant correlation than global Fetuin-A (OG1+OG2+OG3).

Peptide OG3 consists of SEQ ID NO:2 comprising an O-linked oligosaccharide chain bearing two terminal sialic acid residues at position 256 and an O-linked oligosaccharide chain bearing two terminal sialic acid residues at position 270.

Peptide OG2 consists of SEQ ID NO:2 comprising an O-linked oligosaccharide chain bearing one terminal sialic acid residue at position 256 and an O-linked oligosaccharide chain bearing two terminal sialic acid residues at position 270.

TABLE 2

Summary of the main FetuinA tryptic-peptides identified by nanoESI-Qq-TOF MS/MS. Measured (Meas.). Peptide charge state (z). Carbamidomethyl Cys (CAM). Phosphorylation (Phospho). Hexose (Hex). N-acetylhexosamine (HexNAc). Sialic acid (NeuAc). Range, numbering according to the pro-protein sequence.

| Acce-ssion | Chain | SEQ ID NO: | m/z meas. | z | Δ m/z [ppm] | Sequence | Modifications | Glycosyl-ation type | Sialic acid | Range | Label-free MS | Label-free MS (Anova p-value) |
|---|---|---|---|---|---|---|---|---|---|---|---|---|
| FETUA_HUMAN | A | 5 | 1107.041 | 4 | 4.00 | APHGPGLIYRQPNCDDPETEEAALVAIDYINQNLPWGYKH | CAM: 14 | | | 20-57 | | |
| FETUA_HUMAN | A | 6 | 1065.0150 | 4 | 0.79 | PHGPGLIYRQPNCDDPETEEAALVAIDYINQNLPWGYKH | CAM: 12 | | | 21-57 | | |
| FETUA_HUMAN | A | 7 | 1121.8587 | 3 | 4.17 | RQPNCDDPETEEAALVAIDYINQNLPWGYKH | CAM: 4 | | | 29-57 | | |
| FETUA_HUMAN | A | 8 | 1136.0470 | 4 | 2.09 | RQPNCDDPETEEAALVAIDYINQNLPWGYKHTLNQIDEVKV | CAM: 4 | | | 29-67 | | |
| FETUA_HUMAN | A | 9 | 1317.6619 | 2 | 2.97 | DPETEEAALVAIDYINQNLPWGYKH | | | | 35-57 | | |
| FETUA_HUMAN | A | 10 | 971.8927 | 5 | 2.02 | KHTLNQIDEVKVWPQQPSGELFEIEIDTLETTCHVLDPTPVARC | CAM: 32 | | | 58-99 | | |
| FETUA_HUMAN | A | 11 | 1098.3058 | 4 | 2.35 | NQIDEVKVWPQQPSGELFEIEIDTLETTCHVLDPTPVARC | CAM: 28 | | | 62-99 | | |
| FETUA_HUMAN | A | 12 | 508.2569 | 4 | 3.86 | RQLKEHAVEGDCDFQLLKL | CAM: 11 | | | 104-120 | X | ns |
| FETUA_HUMAN | A | 13 | 554.2603 | 3 | 1.70 | KEHAVEGDCDFQLLKL | CAM: 8 | | | 107-120 | X | ns |
| FETUA_HUMAN | A | 14 | 519.2541 | 4 | 1.81 | KEHAVEGDCDFQLLKLDGKF | CAM: 8 | | | 107-124 | X | ns |
| FETUA_HUMAN | A | 15 | 407.2298 | 2 | 1.59 | KFSVVYAKC | | | | 125-131 | X | ns |
| FETUA_HUMAN | A | 16 | 1326.2169 | 3 | 4.29 | KVCQDCPLLAPLNDTRV | CAM: 2, 5; Hex(5)HexNAc(4)NeuAc(2): 14 | N-linked glycan | 2 | 145-159 | X | ns |
| FETUA_HUMAN | A | 16 | 1544.9553 | 3 | 1.03 | KVCQDCPLLAPLNDTRV | CAM: 2, 5; Hex(6)HexNAc(5)NeuAc(3): 14 | N-linked glycan | 2 | 145-159 | X | ns |

TABLE 2-continued

Summary of the main FetuinA tryptic-peptides identified by nanoESI-Qq-TOF MS/MS. Measured (Meas.). Peptide charge state (z). Carbamidomethyl Cys (CAM). Phosphorylation (Phospho). Hexose (Hex). N-acetylhexosamine (HexNAc). Sialic acid (NeuAc). Range, numbering according to the pro-protein sequence.

| Accession | Chain | SEQ ID NO: | m/z meas. | z | Δ m/z [ppm] | Sequence | Modifications | Glycosylation type | Sialic acid | Range | Label-free MS | Label-free MS (Anova p-value) |
|---|---|---|---|---|---|---|---|---|---|---|---|---|
| FETUA_HUMAN | A | 17 | 1183.0825 | 2 | 2.00 | KAALAAFNAQNNGSNFQLEEISRA | | | | 166-187 | | ns |
| FETUA_HUMAN | A | 17 | 1523.9822 | 3 | | KAALAAFNAQNNGSNFQLEEISRA | Hex(5)HexNAc(4) NeuAc(2): 11 | N-linked glycan | 2 | 166-187 | x | ns |
| FETUA_HUMAN | A | 17 | 1143.2366 | 4 | 0.30 | KAALAAFNAQNNGSNFQLEEISRA | Hex(5)HexNAc(4) NeuAc(2): 11 | N-linked glycan | 2 | 166-187 | x | ns |
| FETUA_HUMAN | A | 17 | 1742.7277 | 3 | | KAALAAFNAQNNGSNFQLEEISRA | Hex(6)HexNAc(5) NeuAc(3): 11 | N-linked glycan | 3 | 166-187 | | |
| FETUA_HUMAN | A | 18 | 1290.1579 | 2 | 0.94 | RAQLVPLPPSTVVEFTVSGTDCVAKE | CAM: 21 | | | 188-211 | x | ns |
| FETUA_HUMAN | A | 19 | 1093.8886 | 3 | 1.83 | RAQLVPLPPSTVVEFTVSGTDCVAKEATEAAKC | CAM: 21 | | | 188-218 | | |
| FETUA_HUMAN | A | 20 | 424.2214 | 2 | 0.94 | KCNLLAEKQ | CAM: 1 | | | 219-225 | x | ns |
| FETUA_HUMAN | A | 21 | 401.6823 | 2 | 1.99 | KQYGFCKA | CAM: 5 | | | 226-231 | x | p < 0.05 |
| FETUA_HUMAN | A | 2 | 1741.847 | 5 | 2.91 | LGGAEVAVTCTVFQTQPVTSQPQPEGANEAVPTPVVDPDAPPSPPLGAPGLPPAGSPPDSHVLLAAPPGHQLHR | CAM: 10; Hex(1)HexNAc(1): 19, 33 | O-linked glycan | 2 | 238-311 | x | ns |
| FETUA_HUMAN | A | 2 | 1800.0704 | 5 | 4.71 | LGGAEVAVTCTVFQTQPVTSQPQPEGANEAVPTPVVDPDAPPSPPLGAPGLPPAGSPPDSHVLLAAPPGHQLHR | CAM: 10; Hex(1)HexNAc(1) NeuAc(1): 19 or 33; Hex(1)HexNAc(1) NeuAc(2): 19 or 33 | O-linked glycan | 3 | 238-311 | x | p < 0.01 |
| FETUA_HUMAN | A | 2 | 1858.2795 | 5 | -1.30 | LGGAEVAVTCTVFQTQPVTSQPQPEGANEAVPTPVVDPDAPPSPPLGAPGLPPAGSPPDSHVLLAAPPGHQLHR | CAM: 10; Hex(1)HexNAc(1) NeuAc(2): 19, 33 | O-linked glycan | 4 | 238-311 | x | p < 0.01 |
| FETUA_HUMAN | A | 22 | 724.3871 | 5 | 2.43 | DPDAPPSPPLGAPGLPPAGSPPDSHVLLAAPPGHQLHRA | | | | 275-311 | | |

TABLE 2-continued

Summary of the main FetuinA tryptic-peptides identified by nanoESI-Qq-TOF MS/MS. Measured (Meas.). Peptide charge state (z). Carbamidomethyl Cys (CAM). Phosphorylation (Phospho). Hexose (Hex). N-acetylhexosamine (HexNAc). Sialic acid (NeuAc). Range, numbering according to the pro-protein sequence.

| Accession | Chain | SEQ ID NO: | m/z meas. | z | Δ m/z [ppm] | Sequence | Modifications | Glycosylation type | Sialic acid | Range | Label-free MS | Label-free MS (Anova p-value) |
|---|---|---|---|---|---|---|---|---|---|---|---|---|
| FETUA_HUMAN | A | 23 | 387.6989 | 2 | 0.09 | RAHYDLRH | | | | 312-317 | X | ns |
| FETUA_HUMAN | A | 24 | 568.0879 | 5 | 5.50 | RAHYDLRHTFMGVVSLGSPSGEVSHPRK | | | | 312-337 | | |
| FETUA_HUMAN | A | 25 | 642.3136 | 3 | 2.16 | RHTFMGVVSLGSPSGEVSHPR | | | | 318-336 | | |
| FETUA_HUMAN | A | 26 | 694.3468 | 3 | 1.16 | RHTFMGVVSLGSPSGEVSHPRK | | | | 318-337 | X | ns |
| FETUA_HUMAN | A | 26 | 541.0047 | 4 | 3.36 | RHTFMGVVSLGSPSGEVSHPRK | Phospho: 13 | | | 318-337 | X | ns |
| FETUA_HUMAN | A | 26 | 721.0030 | 3 | 2.16 | RHTFMGVVSLGSPSGEVSHPRK | Phospho: 13 | | | 318-337 | X | ns |
| FETUA_HUMAN | A | 27 | 553.0377 | 4 | 5.00 | RHTFMGVVSLGSPSGEVSHPRKT | | | | 318-338 | | |
| FETUA_HUMAN | B | 28 | 1008.5432 | 2 | 4.76 | RTVVQPSVGAAAGPVVPPCPGRI | CAM: 18 | | | 341-361 | X | ns |
| FETUA_HUMAN | B | 28 | 1336.6567 | 2 | 3.40 | RTVVQPSVGAAAGPVVPPCPGRI | CAM: 18; Hex(1)HexNAc(1)NeuAc(1): 1 | O-linked glycan | 1 | 341-361 | X | ns |
| FETUA_HUMAN | B | 28 | 891.4380 | 3 | 0.90 | RTVVQPSVGAAAGPVVPPCPGRI | CAM: 18; Hex(1)HexNAc(1)NeuAc(1): 1 | O-linked glycan | 1 | 341-361 | X | ns |
| FETUA_HUMAN | B | 28 | 988.4692 | 3 | 0.14 | RTVVQPSVGAAAGPVVPPCPGRI | CAM: 18; Hex(1)HexNAc(1) | O-linked glycan | 2 | 341-361 | X | p < 0.01 |
| FETUA_HUMAN | B | 29 | 958.0155 | 2 | 0.94 | TVVQPSVGAAAGPVVPPCPGRI | CAM: 17 | | | 342-361 | | |
| FETUA_HUMAN | B | 30 | 908.4811 | 2 | 0.81 | VVQPSVGAAAGPVVPPCPGRI | CAM: 16 | | | 343-361 | | |

The pertinence of the polypeptide OG3 was further assessed by a receiver operating characteristic (ROC) analysis. The ROC curve of OG3 levels of 42 active patients divided in 2 subgroups based on a percentage of improvement in ARTSS of 50% is shown in FIG. 9A. The AUC was of 0.7015 (with p-value of 0.03509). The ROC curve of OG3 levels of 42 active patients divided in 2 subgroups based on a percentage of improvement in ARTSS=10%, % is shown in FIG. 9B. The AUC was of 0.7978 (with p-value of 0.0095). In these ROC curves, controls are defined as responder patients (i.e. patients with a percentage of improvement in ARTSS greater than or equal to the percentage of ARTSS improvement thresholds defined above).

Moreover ROC curve of OG3 levels of 42 active patients divided in 2 subgroups based on a percentage of improvement in ARTSS of 50% and in which the controls are defined as non-responder patients (i.e. patients with a percentage of improvement in ARTSS lower than 50%) is shown in FIG. 13.A. The AUC was of 0.7015 (with p-value of 0.03509). The ROC curve of OG3 levels of 42 active patients divided in 2 subgroups based on a percentage of improvement in ARTSS of 43.9% and in which the controls are defined as non-responder patients (i.e. patients with a percentage of improvement in ARTSS lower than 43.9%) is shown in FIG. 13.B. The AUC was of 0.8050 (with p-value of 0.0007). The ROC curve of OG3 levels of 42 active patients divided in 2 subgroups based on a percentage of improvement in ARTSS of 10% and in which the controls are defined as non-responder patients (i.e. patients with a percentage of improvement in ARTSS lower than 10%) is shown in FIG. 13.C. The AUC was of 0.7978 (with p-value of 0.0095).

These latter ROC curves in which the controls are defined as non-responder patients were associated with the following data on sensitivity and specificity.

TABLE 3

Threshold at 10% improvement in ARTSS

| Cutoff OG3 | Sensitivity % | Specificity % |
|---|---|---|
| >8619 | 100 | 12.5 |
| >9377 | 100 | 25 |
| >10984 | 100 | 37.5 |
| >14446 | 100 | 50 |
| >20117 | 97.06 | 50 |
| >23537 | 97.06 | 62.5 |
| >23893 | 94.12 | 62.5 |
| >24170 | 91.18 | 62.5 |
| >24893 | 88.24 | 62.5 |
| >26369 | 85.29 | 62.5 |
| >27576 | 82.35 | 62.5 |
| >28037 | 79.41 | 62.5 |
| >28520 | 76.47 | 62.5 |
| >28950 | 73.53 | 62.5 |
| >29308 | 70.59 | 62.5 |
| >30786 | 67.65 | 62.5 |
| >32026 | 64.71 | 62.5 |
| >32918 | 61.76 | 62.5 |
| >33777 | 58.82 | 62.5 |
| >34916 | 55.88 | 62.5 |
| >36447 | 55.88 | 75 |
| >37862 | 52.94 | 75 |
| >39205 | 50 | 75 |
| >41113 | 50 | 87.5 |
| >43103 | 47.06 | 87.5 |
| >43967 | 44.12 | 87.5 |
| >45310 | 41.18 | 87.5 |
| >46825 | 38.24 | 87.5 |
| >48242 | 35.29 | 87.5 |
| >49345 | 35.29 | 100 |
| >50051 | 32.35 | 100 |
| >50788 | 29.41 | 100 |

TABLE 3-continued

Threshold at 10% improvement in ARTSS

| Cutoff OG3 | Sensitivity % | Specificity % |
|---|---|---|
| >51984 | 26.47 | 100 |
| >57652 | 23.53 | 100 |
| >62528 | 20.59 | 100 |
| >62952 | 17.65 | 100 |
| >64570 | 14.71 | 100 |
| >67985 | 11.76 | 100 |
| >71033 | 8.824 | 100 |
| >73660 | 5.882 | 100 |
| >83772 | 2.941 | 100 |

TABLE 4

Threshold at 43.9% improvement in ARTSS

| Cutoff OG3 | Sensitivity % | Specificity % |
|---|---|---|
| >8619 | 100 | 4.762 |
| >9377 | 100 | 9.524 |
| >10984 | 100 | 14.29 |
| >14446 | 100 | 19.05 |
| >20117 | 95.24 | 19.05 |
| >23537 | 95.24 | 23.81 |
| >23893 | 95.24 | 28.57 |
| >24170 | 95.24 | 33.33 |
| >24893 | 95.24 | 38.1 |
| >26369 | 95.24 | 42.86 |
| >27576 | 90.48 | 42.86 |
| >28037 | 90.48 | 47.62 |
| >28520 | 90.48 | 52.38 |
| >28950 | 90.48 | 57.14 |
| >29308 | 85.71 | 57.14 |
| >30786 | 80.95 | 57.14 |
| >32026 | 80.95 | 61.9 |
| >32918 | 80.95 | 66.67 |
| >33777 | 76.19 | 66.67 |
| >34916 | 76.19 | 71.43 |
| >36447 | 76.19 | 76.19 |
| >37862 | 71.43 | 76.19 |
| >39205 | 71.43 | 80.95 |
| >41113 | 71.43 | 85.71 |
| >43103 | 66.67 | 85.71 |
| >43967 | 61.9 | 85.71 |
| >45310 | 57.14 | 85.71 |
| >46825 | 52.38 | 85.71 |
| >48242 | 47.62 | 85.71 |
| >49345 | 47.62 | 90.48 |
| >50051 | 42.86 | 90.48 |
| >50788 | 38.1 | 90.48 |
| >51984 | 33.33 | 90.48 |
| >57652 | 28.57 | 90.48 |
| >62528 | 23.81 | 90.48 |
| >62952 | 19.05 | 90.48 |
| >64570 | 19.05 | 95.24 |
| >67985 | 19.05 | 100 |
| >71033 | 14.29 | 100 |
| >73660 | 9.524 | 100 |
| >83772 | 4.762 | 100 |

TABLE 5

Threshold at 50% improvement in ARTSS

| Cutoff | Sensitivity % | Specificity % |
|---|---|---|
| >8619 | 100 | 3.571 |
| >9377 | 100 | 7.143 |
| >10984 | 100 | 10.71 |
| >14446 | 100 | 14.29 |
| >20117 | 92.86 | 14.29 |
| >23537 | 92.86 | 17.86 |
| >23893 | 92.86 | 21.43 |

TABLE 5-continued

Threshold at 50% improvement in ARTSS

| Cutoff | Sensitivity % | Specificity % |
|---|---|---|
| >24170 | 92.86 | 25 |
| >24893 | 92.86 | 28.57 |
| >26369 | 92.86 | 32.14 |
| >27576 | 92.86 | 35.71 |
| >28037 | 92.86 | 39.29 |
| >28520 | 92.86 | 42.86 |
| >28950 | 92.86 | 46.43 |
| >29308 | 85.71 | 46.43 |
| >30786 | 78.57 | 46.43 |
| >32026 | 78.57 | 50 |
| >32918 | 78.57 | 53.57 |
| >33777 | 78.57 | 57.14 |
| >34916 | 78.57 | 60.71 |
| >36447 | 78.57 | 64.29 |
| >37862 | 71.43 | 64.29 |
| >39205 | 71.43 | 67.86 |
| >41113 | 71.43 | 71.43 |
| >43103 | 64.29 | 71.43 |
| >43967 | 64.29 | 75 |
| >45310 | 57.14 | 75 |
| >46825 | 50 | 75 |
| >48242 | 42.86 | 75 |
| >49345 | 42.86 | 78.57 |
| >50051 | 35.71 | 78.57 |
| >50788 | 28.57 | 78.57 |
| >51984 | 21.43 | 78.57 |
| >57652 | 21.43 | 82.14 |
| >62528 | 21.43 | 85.71 |
| >62952 | 14.29 | 85.71 |
| >64570 | 14.29 | 89.29 |
| >67985 | 14.29 | 92.86 |
| >71033 | 7.143 | 92.86 |
| >73660 | 7.143 | 96.43 |
| >83772 | 7.143 | 100 |

These results confirm that OG3 is useful to discriminate clinical responders from non-responders before AIT.

Figure 10:
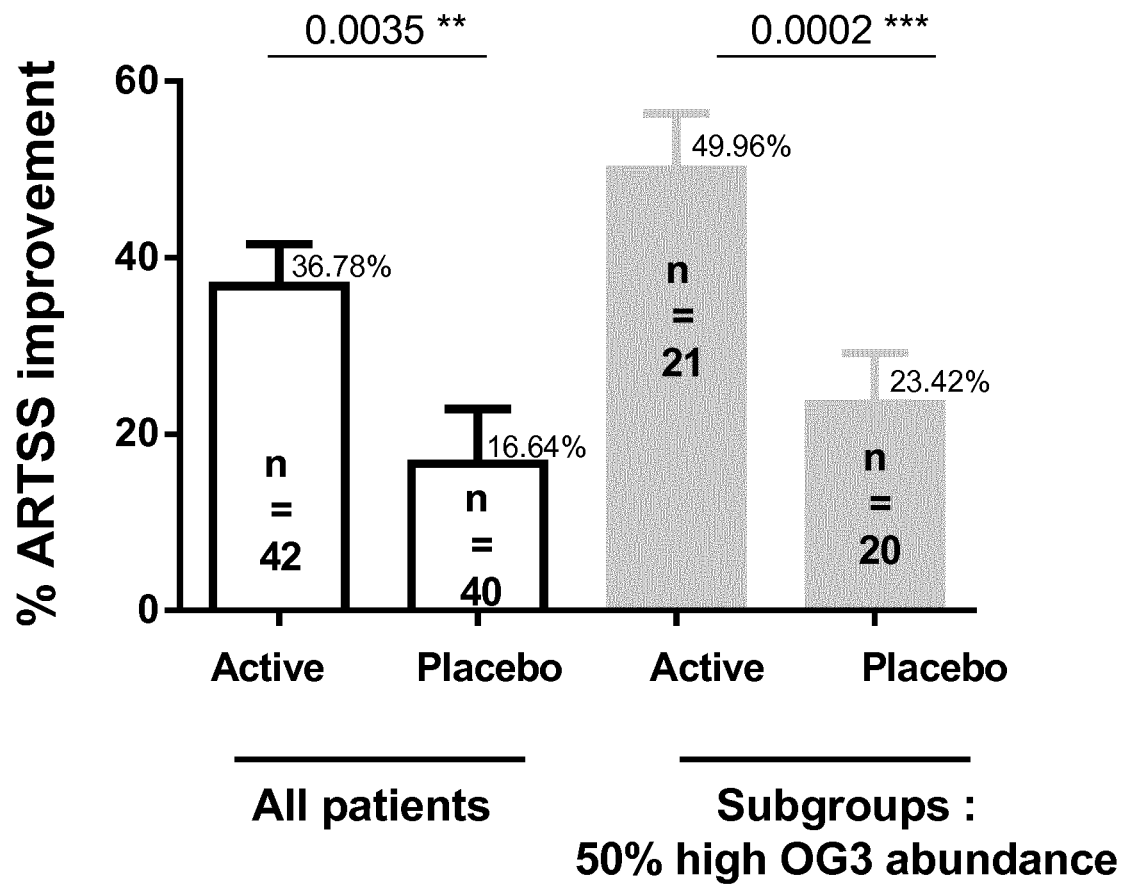
FIG. 10: Patients exclusion based on OG3 abundance and its impact on clinical efficacy. "50% High OG3 abundance" subgroups represent patients from active and placebo groups for which peptide abundances before treatment are higher than the median value of OG3 abundance calculated for all patients (i.e. from both active and placebo groups) Median OG3 Abundance=36301. OG3 consists of SEQ ID NO:2 comprising an O-linked oligosaccharide chain bearing two terminal sialic acid residues at position 256 and an O-linked oligosaccharide chain bearing two terminal sialic acid residues at position 270). Percentages of ARTSS improvement are shown as mean±SEM in active and placebo groups. Mean variations between active and placebo are tested with a Mann-Whitney statistical test.

Finally, patients from each treatment group (i.e. active and placebo) were divided into 2 subgroups depending upon levels of OG3 found in their plasma before treatment (subgroups "50% high OG3 abundance"). 50% High OG3 abundance" subgroups represent patients from active and placebo groups for which peptide abundances before treatment are higher than the median value of OG3 abundance calculated for all patients (i.e. from both active and placebo groups) Median OG3 Abundance=36301. As shown in FIG. 10, a more pronounced improvement in clinical symptoms was observed in active patients who had the 50% highest OG3 levels.

Sialylated Fetuin-A Synergizes with LPS in a TLR4-Dependent Pathway

Functional interactions between sialylated Fetuin-A and TLR4 were examined using HEK-293 cells expressing human TLR4 and an inducible secreted embryonic alkaline phosphatase as a reporter gene. Those cells were stimulated with either LPS, sialylated Fetuin-A at various doses, or a mixture of both. As shown in FIG. 11,a, sialylated Fetuin-A alone had no effect, whereas a combination of sialylated Fetuin-A and LPS acted in synergy to activate TLR4 in a dose-dependent manner.

Since dendritic cells (DCs) are critical for T cell priming against allergens, and with the notion that bacterial LPS is an important sensitization cofactor, it was then examined the capacity of sialylated Fetuin-A to synergize with LPS and/or allergens, to impact DC polarization. MoDCs generated in serum-free medium were incubated with either LPS, sialylated Fetuin-A at various doses, or a combination of both. Stimulation of MoDCs with a mixture of LPS and sialylated Fetuin-A enhanced the expression of CD83 and CD86, and to a lower extent of CD80 co-stimulatory molecules (FIG. 11,b), whereas LPS or sialylated Fetuin-A alone had no effect. Similarly, a combination of the two molecules increased the secretion of IL-6, IL-10, IL-12 p-70 and TNF-α cytokines, when compared with LPS alone, whereas sialylated Fetuin-A per se had no activity (FIG. 11,c). No stimulation of MoDCs was observed in presence of α-(2→3, 6,8,9)-Neuraminidase, desialylation buffer or free sialic acids (data not shown). Noteworthy, the synergy observed between LPS and sialylated Fetuin-A was totally abrogated by adding the TLR4 antagonist LPS-RS (FIG. 11,b-c), establishing that sialylated Fetuin-A and LPS synergized to activate the TLR4 pathway.

Sialylated Fetuin-A and Neuraminidase-treated sialylated Fetuin-A (i.e. desialylated Fetuin-A) were subsequently compared for their capacity to synergize with LPS in those human cellular assays. The synergistic modulation of TLR4 activity by LPS was substantially decreased when hTLR4 HEK-293 cells were co-stimulated with desialylated Fetuin-A as opposed to sialylated Fetuin-A (FIG. 11,d). Consistent with this observation, no synergistic effect was observed between LPS and desialylated Fetuin-A on MoDCs, both in terms of the induction of co-stimulatory molecules (FIG. 11,e) and cytokine secretion (FIG. 11,f). Collectively, our results establish the synergistic activation of the TLR4 pathway by LPS and FetA, with evidence for sialylation of the latter in this functional interaction.

Sialylated Fetuin-A, but not Desialylated Fetuin-A, Enhances the Pro-Allergic Features of Type 2 MoDCs (DC2s)

Engagement of TLR4 is known to contribute to allergic inflammation, for example during concomitant exposure to allergens with endotoxins, or as a consequence of a functional mimicry of MD2 by the allergen. It was investigated the potential contribution of sialylated Fetuin-A glycoforms to such TLR4-mediated allergic inflammation. Immature MoDCs were polarized towards a DC2 phenotype (i.e. capable to polarize naïve CD4$^+$ T cells towards IL-5 and IL-13 secreting T$_H$2 cells), using a mixture of TSLP, IL-25, IL-33 and low doses (i.e. 10 ng/mL) of LPS, in presence of 10 µg/mL sialylated Fetuin-A or desialylated Fetuin-A, respectively. A flow cytometry analysis revealed an up-regulation of CD83 and CD86 co-stimulatory markers in presence of sialylated Fetuin-A but not desialylated Fetuin-A (FIG. 12,a). Similarly, DC2s differentiated in presence of sialylated Fetuin-A secreted higher levels of IL-6, IL-8, IL-10 and TNF-α (FIG. 12,b), when compared to DC2s treated with desialylated Fetuin-A. The latter observation was further confirmed when monitoring the expression of genes specifically associated with a DC2 polarization, such as PADI2, GATA3 and NMES. Such DC2 marker genes were overexpressed in presence of sialylated Fetuin-A but not desialylated Fetuin-A. In contrast, the expression of genes rather associated with DC1 or regulatory DCs, such as MX1 or C1QA, respectively, was highly down-regulated when DC2s were cultured in the presence of sialylated Fetuin-A, but not desialylated Fetuin-A (FIG. 12,c). In addition, following a stimulation of DC2s with a combination of aqueous allergen extracts and sialylated Fetuin-A or desialylated Fetuin-A, sialylated Fetuin-A synergized with a grass pollen extract to induce the secretion of IL-6, IL-8, IL-10 and TNF-α cytokines (FIG. 12,d), whereas no such effect was observed with desialylated Fetuin-A. Similarly, DCs cultured with house dust mite (HDM) allergen extract secreted higher amounts of IL-6, IL-10, and TNF-α in presence of sialylated Fetuin-A, whereas this synergy was not observed with desialylated Fetuin-A (FIG. 12,*e*). No clear influence of sialylated Fetuin-A or desialylated Fetuin-A was observed on IL-8 secretion, already very high in presence of house dust mites allergens. Collectively, those experiments established that sialylated Fetuin-A can enhance the proallergic profile of DC2s in presence of natural allergens, in relationship with sialylation levels of the Fetuin-A molecule.

Example 3

Clinical Samples from House Dust Mite Study

Study Design

The objectives of this multicenter, double-blind, parallel-group comparative study were to evaluate the efficacy and safety of the house dust mite extract in patients with perennial allergic rhinitis due to house dust mite. Patients were randomized to receive house dust mite extract at dose A, house dust mite extract at dose B or a placebo tablets. Patients were treated over a period of 12 months. Serum samples were collected and symptoms monitored at weeks 0, 16 and 52.

Serum Analysis

Serum samples (340 μL each) were processed using a human Multiple Affinity Removal System (MARS) Human 14 (Hu-14 column, 10×100 mm, Agilent Technologies, Palo Alto, USA), which selectively removes α1-acid glycoprotein, α1-antitrypsin, α2-macroglobuin, albumin, apolipoprotein A1, apolipoprotein A2, complement C3, fibrinogen, haptoglobin, IgA, IgG, IgM, transferrin, and transthyretin. An Ultimate 3000 HPLC apparatus (Thermo scientific, Waltham, USA) was used for the affinity depletion. Flow-through proteins were collected and concentrated according to the manufacturer's instructions. Following depletion, samples were stored at −80° C. until analysis. The run-to-run reproducibility of depletion was confirmed by chromatography and SDS-PAGE analyses under reducing conditions, using 4-12% NuPAGE gels (Thermo scientific).

The invention claimed is:

1. A method for treating a patient by immunotherapy which comprises the steps of:
   1) selecting a patient for immunotherapy by:
      a) detecting the level of expression of a Fetuin-A polypeptide, or a fragment thereof, comprising an O-linked oligosaccharide chain bearing two terminal sialic acid residues at position 256 and comprising an O-linked oligosaccharide chain bearing two terminal sialic acid residues at position 270, by reference to the amino acid positions as shown in sequence SEQ ID NO:1, in a biological sample from said patient;
      b) comparing said level of expression with a control; and
      c) selecting or rejecting said patient for immunotherapy based on the comparison with the control;
      wherein said biological sample is taken before the commencement of immunotherapy, and wherein said immunotherapy comprises administration of an allergen or auto-antigen to said patient in order to treat allergy or auto-immune disease; and
   2) administering said allergen or auto-antigen to said patient selected at step c).

2. The method for treating a patient by immunotherapy of claim 1, wherein step c) is performed by selecting patient for immunotherapy when the level of expression of said Fetuin-A polypeptide, or fragment thereof in the patient sample is equal to or greater than the level of expression in the control, and the control is derived from:
   (i) a responder subject or group of responder subjects known to respond to said immunotherapy;
   (ii) a non-responder subject or group of non-responder subjects; or
   (iii) a randomly selected group of subjects.

3. The method for treating a patient by immunotherapy of claim 1, wherein
   (i) at least 0.0046% of the total peptide abundance in the control consists of the peptide SEQ ID N0:2 comprising an O-linked oligosaccharide chain bearing two terminal sialic acid residues at position 256 and an 0-linked oligosaccharide chain bearing two terminal sialic acid residues at position 270, or
   (ii) at least 3,600 units of relative peptide abundance in the control consists of the peptide SEQ ID NO:2 comprising an O-linked oligosaccharide chain bearing two terminal sialic acid residues at position 256 and an 0-linked oligosaccharide chain bearing two terminal sialic acid residues at position 270, and
   wherein the step of detecting the level of expression of said Fetuin-A polypeptide or fragment thereof is determined by:
   (A) depleting a serum sample in albumin, IgG, antitrypsin, IgA, transferrin and haptoglobulin;
   (B) degrading with trypsin the depleted serum sample; and
   (C) quantifying the relative abundance in said trypsin-digested depleted serum sample of the peptide SEQ ID NO:2, comprising an O-linked oligosaccharide chain bearing two terminal sialic acid residues at position 256 and an O-linked oligosaccharide chain bearing two terminal sialic acid residues at position 270, by LC-MS/MS.

4. The method for treating a patient by immunotherapy of claim 1, wherein the immunotherapy comprises administration of allergen to a mucosal surface.

5. The method for treating a patient by immunotherapy of claim 1, wherein the immunotherapy comprises administration of allergen via sublingual route.

6. The method for treating a patient by immunotherapy of claim 1, wherein the patient has grass pollen allergy and the immunotherapy comprises administration of grass pollen allergen.

7. The method for treating a patient by immunotherapy of claim 1, wherein the patient has grass pollen allergy and the immunotherapy comprises administration of 5-grass-pollen extracts from pollen of *Dactylis, Poa, Lolium, Anthoxanthum* and *Phleum* genera.

8. The method for treating a patient by immunotherapy of claim 1, wherein the patient has grass pollen allergy and the immunotherapy comprises sublingual administration of 5-grass-pollen extracts from pollen of *Dactylis, Poa, Lolium, Anthoxanthum* and *Phleum* genera.

* * * * *